(12) United States Patent
Adams et al.

(10) Patent No.: US 7,189,745 B1
(45) Date of Patent: *Mar. 13, 2007

(54) COMPOUNDS

(75) Inventors: Jerry L. Adams, Wayne, PA (US); Neil W. Johnson, Downingtown, PA (US); Jeffrey H. Murray, Norristown, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/130,018

(22) PCT Filed: Nov. 20, 2000

(86) PCT No.: PCT/US00/31791

§ 371 (c)(1),
(2), (4) Date: May 10, 2002

(87) PCT Pub. No.: WO01/37835

PCT Pub. Date: May 31, 2001

Related U.S. Application Data

(60) Provisional application No. 60/166,886, filed on Nov. 22, 1999, provisional application No. 60/166,885, filed on Nov. 22, 1999, provisional application No. 60/166,814, filed on Nov. 22, 1999, provisional application No. 60/166,895, filed on Nov. 22, 1999.

(51) Int. Cl.
 A61K 31/4439 (2006.01)
 C07D 401/04 (2006.01)

(52) U.S. Cl. .................... 514/341; 546/274.1

(58) Field of Classification Search ................ 514/341; 546/274.1
See application file for complete search history.

(56) References Cited

U.S. PATENT DOCUMENTS

| | | | |
|---|---|---|---|
| 3,707,475 A | 12/1972 | Lombardino | |
| 3,940,486 A | 2/1976 | Fitzi | |
| 4,348,404 A | 9/1982 | Whitney | |
| 4,447,431 A | 5/1984 | Sallmann | |
| 5,166,214 A | 11/1992 | Billheimer et al. | |
| 5,179,117 A | 1/1993 | Maduskuie, Jr. | |
| 5,236,917 A | 8/1993 | Dunlap et al. | |
| 5,310,748 A | 5/1994 | Wilde et al. | |
| 5,514,505 A | 5/1996 | Limburg et al. | |
| 5,552,557 A | 9/1996 | Fujii et al. | |
| 5,620,999 A | 4/1997 | Weier et al. | |
| 5,656,644 A | 8/1997 | Adams et al. | |
| 5,717,100 A | 2/1998 | Selnick et al. | |
| 5,859,041 A | 1/1999 | Liverton et al. | |
| 6,040,320 A | 3/2000 | Beers et al. | |
| 6,207,687 B1 | 3/2001 | Claiborne et al. | |
| 6,235,760 B1 | 5/2001 | Feuerstein | |
| 6,342,510 B1 | 1/2002 | Isakson et al. | |
| 6,436,966 B1 | 8/2002 | Ohkawa et al. | |
| 6,548,520 B1* | 4/2003 | Adams et al. | 514/341 |
| 6,602,877 B1 | 8/2003 | Banborough et al. | |
| 2003/0134837 A1 | 7/2003 | Gaiba et al. | |
| 2003/0153588 A1 | 8/2003 | Steadman et al. | |
| 2004/0038964 A1 | 2/2004 | Dean et al. | |
| 2004/0053943 A1 | 3/2004 | Adams et al. | |
| 2004/0127496 A1 | 7/2004 | Dean et al. | |
| 2004/0192689 A1 | 9/2004 | Dean et al. | |
| 2004/0198730 A1 | 10/2004 | Dean et al. | |
| 2004/0209883 A1 | 10/2004 | Bamford et al. | |
| 2004/0235843 A1 | 11/2004 | Bamford et al. | |
| 2004/0248896 A1 | 12/2004 | Dean et al. | |
| 2004/0254186 A1 | 12/2004 | Dean et al. | |

FOREIGN PATENT DOCUMENTS

| | | |
|---|---|---|
| WO | WO 97/36587 | 10/1997 |
| WO | WO 98/16227 | 4/1998 |
| WO | WO 99/01449 | 1/1999 |
| WO | WO 99/32436 | 7/1999 |
| WO | WO 99/32455 | 7/1999 |
| WO | WO 99/061437 | 12/1999 |
| WO | WO 00/01688 | 1/2000 |
| WO | WO 00/26209 | 5/2000 |
| WO | WO 00/33836 | 6/2000 |
| WO | WO 00/64422 | 11/2000 |
| WO | WO 01/37835 | 5/2001 |
| WO | WO 01/38324 | 5/2001 |

OTHER PUBLICATIONS

CA 130:95507, Claiborne et al. 1998.*
CA 135:19656, Dean et al. 2001.*
Revesz, "Anti-inflammatory 4-phenyl-5-pyrimidinyl-imidazoles and their preparation, compositions, and use", Abstract WO 2000026209, May 11, 2000, AN 2000:314693.
"Preparation of pyridinylimidazoles for treatment of DSBP kinase mediated disease", Abstract WO 9961437, Dec. 2, 1999, AN 1999:764034.
Adams et al., *Bioorganic & Medicinal Chemistry Letters*, vol. 8 pp. 3111-3116 (1998).
Adams et al., *Current Opinion in Drug Discovery and Development*, vol. 2(2) pp. 96-109 (1999).
Antolini et al., *Bioorganic & Medicinal Chemistry Letters*, vol. 9 pp. 1023-1028 (1999).

(Continued)

*Primary Examiner*—Patricia L. Morris
(74) *Attorney, Agent, or Firm*—Dara L. Dinner; Stephen Venetianer; Charles M. Kinzig

(57) ABSTRACT

The present invention is directed to novel compounds of Formula (I) for use in the treatment of diseases, in a mammal, in which inappropriate, excessive or undesirable angiogenesis has occurred and/or where excessive Tie2 receptor activity has occurred.

15 Claims, No Drawings

OTHER PUBLICATIONS

Astles et al., *J. Med. Chem.*, vol. 39 pp. 1423-1432 (1996).
Bilodeau et al., *J. Org. Chem.*, vol. 63 pp. 2800-2801 (1998).
Boehm et al., *Exp Opinion Ther. Patents*, vol. 10(1) pp. 25-37 (2000).
Boehm et al., *J. Med Chem.*, vol. 39 pp. 3929-3937 (1996).
Claiborne et al., *Tetrahedron Letters*, vol. 39 pp. 8939-8942 (1998).
Cuenda et al., *FEBS Letters*, vol. 364 pp. 229-233 (1995).
de Laszlo et al., *Bioorganic & Medical Chemistry Letters*, vol. 8 pp. 2689-2694 (1998).
Dumas et al., *Bioorganic & Medical Chemistry Letters*, vol. 10 pp. 2047-2050 (2000).
Dumas et al., *Bioorganic & Medical Chemistry Letters*, vol. 10 2051-2054 (2000).
Eberwein et al., *Clinical Cancer Researc*, vol. 6 (Supple.) Poster session 17 p. 4547(406) (Nov. 2000).
Engel et al., *Liebigs Ann. Chem.*, p. 1916-1927 (1978).
Fischer et al., *Rec.Trav.Chim.Pays.Bas.*, vol. 84 p. 439-440 (1965).
Gallagher et al., *Bioorganic & Medical Chemistry*, vol. 5(1) pp. 49-64 (1997).
Garcia-Echeverria et al., *Med. Res. Reviews*, vol. 20(1) pp. 28-57 (2000).
Garigipati, R., *Tetrahedron Letters*, vol. 31(14) pp. 1969-1972 (1990).
Hall-Jackson et al., *Oncogene*, vol. 18 pp. 2047-2054 (1999).
Heimbrock et al., "Identification of Potent, Selective Inhibitors of Raf Protein Kinase," *Amer. Assoc for Cancer Res New Orleans* Abstract 3793 Apr. 1998.
Henry et al., *Bioorganic & Medical Chemistry Letters*, vol. 8 pp. 3335-3340 (1998).
Henry et al., *Drugs of the Future*, vol. 24(12) pp. 1345-1354 (1999).
Ishibashi, *Chem. Pharm. Bull.*, vol. 37(8), pp. 2214-2216 (1989).
Johnson, *J. Chem.Soc.*, Perkin Trans., vol. 1, pp. 895-905 (1996).
Katritzky, *Synthesis*, pp. 45-47 (1993).
Minato et al., *Tetrahedron Letters*, vol. 22, p. 5319-5322 (1981).
Lackey et al., *Bioorganic & Medical Chemistry Letters*, vol. 10 pp. 223-226 (2000).
Lee et al., *Pharmacol Ther.*, vol. 82(2-3) pp. 389-397 (1999).
Lisnock et al., *BioChemistry*, vol. 37 pp. 16573-16581 (1998).
Liverton et al., *J. Med Chem.*, vol. 42 pp. 2180-2190 (1999).
Lowinger et al., Clinical Cancer Research, vol. 6(No. 335) (Suppl.) Poster session 13 p. 4533 (Nov. 2000).
Morton et al., *Tetrahedron Letters*, 4123-4124 (1982).
Pridgen, *J. Org.Chem.*, vol. 47, p. 4319-4323 (1982).
R.P.Soni, *Aust.J.Chem.*, vol. 35, p. 1493-6 (1982).
Revesz et al., *Bioorganic & Medical Chemistry Letters*, vol. 10 pp. 1261-1264 (2000).
Salituro et al., *Current Medicinal Chemistry*, vol. 6 pp. 807-823 (1999).
Alves, et al., *Tetrahedron Letters*, vol. 29, pp. 2135-2136 (1988).
Echavarres et al., *J.Amer.Chem.Soc.*, vol. 109, pp. 5478-5486 (1978).
Stover et al., *Current Opinion in Drug Discovery and Development*, vol. 2(4) pp. 274-285 (1999).
Strzybny et al., *J. Org. Chem.*, vol. 28, pp. 3381-3383 (1963).
Ishikura et al., M., *Chem.Pharm.Bull.*, vol. 11, pp. 4755-4757 (1985).
Thompson, et al., *J.Org.Chem.*, vol. 49, pp. 5237-5243 (1984).
Toledo et al., *Current Medicinal Chemistry*, vol. 6 pp. 775-805 (1999).
Tong et al., *Nature Structural Biology*, vol. 4(4) pp. 311-316 (1997).
Ashley Publications, "Two Novel structural classes of p38 Kinase inhibitors," *Exp Opin. Ther. Patents* vol. 9(4) pp. 477-480 (1999).
Uno, *Bull. Chem. Soc. Japan.*, vol. 69, pp. 1763-1767 (1996).
VanLeusen et al., *J.O.C.*, vol. 42 (7) pp. 1153-1159 (1977).
Ashley Publications, "p38 Inhibitors based on the pyridylurea and pyridylacetoamide templates," *Exp Opin. Ther. Patents*, vol. 10(7) pp. 1151-1154 (2000).
Wang et al., *Structure*, vol. 6(9) pp. 1117-1128 (Sep. 15, 1998).
Young et al., *The Journal of Biological Chemistry*, vol. 272(18) pp. 12116-12121 (1997).
Zavyalov, et al., *Khim Farm Zh*, vol. 26(3), p. 88 (1992) (With Translation).

* cited by examiner

COMPOUNDS

This is a §371 national stage filing of International Application PCT/US00/31791, filed 20 Nov. 2000, which claims benefit from the following Provisional Applications: 60/166,886 filed 22 Nov. 1999, 60/166,885 filed 22 Nov. 1999, 60/166,814 filed 22 Nov. 1999 and 60/166,895 filed 22 Nov. 1999.

FIELD OF THE INVENTION

The present invention relates to the treatment of diseases, in a mammal, in which inappropriate, excessive or undesirable angiogenesis has occurred and/or where excessive Tie2 receptor activity has occurred.

BACKGROUND OF THE INVENTION

Chronic proliferative diseases are often accompanied by profound angiogenesis, which can contribute to or maintain an inflammatory and/or proliferative state, or which leads to tissue destruction through the invasive proliferation of blood vessels. (Folkman, EXS 79:1–8, 1997; Folkman, *Nature Medicine* 1:27–31, 1995; Folkman and Shing, *J. Biol. Chem.* 267:10931, 1992).

Angiogenesis is generally used to describe the development of new or replacement blood vessels, or neovascularisation. It is a necessary and physiological normal process by which the vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott, *Ann. Rheum. Dis.*, 51, 919,1992). In diabetes (and in many different eye diseases), new vessels invade the macula or retina or other ocular structures, and may cause blindness (Brooks et al., *Cell*, 79, 1157, 1994). The process of atherosclerosis has been linked to angiogenesis (Kahlon et al., *Can. J. Cardiol.* 8, 60, 1992). Tumor growth and metastasis have been found to be angiogenesis-dependent (Folkman, *Cancer Biol*, 3, 65, 1992; Denekamp, *Br. J. Rad.* 66, 181, 1993; Fidler and Ellis, *Cell*, 79, 185, 1994).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly et al., *Cell*, 79, 315, 1994; Ingber et al., *Nature*, 348, 555, 1990), ocular diseases (Friedlander et al., *Science*, 270, 1500, 1995), arthritis (Peacock et al., *J. Exp. Med.* 175, 1135, 1992; Peacock et al., *Cell. Immun.* 160, 178, 1995) and hemangioma (Taraboletti et al., *J. Natl. Cancer Inst.* 87, 293, 1995).

Angiogenesis signals result from the interaction of specific ligands with their receptors. The Tie1 and Tie2 receptors are single-transmembrane, tyrosine kinase receptors (Tie stands for Tyrosine kinase receptors with immunoglobulin and EGF homology domains). Both were recently cloned and reported by several groups (Dumont et al., *Oncogene* 8:1293–1301, 1993; Partanen et al., Mol. Cell Biol. 12:1698–1707, 1992; Sato et al., *Proc. Natl. Acad. Sci. USA* 90:0355–9358, 1993).

Based upon the importance of Tie2 receptors in angiogenesis, inhibition of Tie2 kinase activity is predicted to interrupt angiogenesis, providing disease-specific therapeutic effects. Recently, Lin et al. (*J. Clin. Invest.* 100:2072–2078, 1997) has shown that exogenously administered soluble Tie2 receptor inhibited angiogenesis and cancer growth in animal models. Thus inhibition of Tie2 receptors by other means, such as inhibition of Tie2 receptor kinase activity, is expected to have therapeutic benefit in proliferative diseases involving angiogenesis.

The current application teaches the novel finding that compounds of specific structure can inhibit the kinase activity of the Tie2 receptor, block its signal transduction and thus may be beneficial for proliferative diseases via inhibition of signals for angiogenesis.

SUMMARY OF THE INVENTION

The present invention is directed to novel compounds of Formula (I), and pharmaceutical compositions comprising a compound of Formula (I) and a pharmaceutically acceptable diluent or carrier.

Another aspect of the present invention is the use of compounds of Formula (I) as Tie2 receptor kinase inhibitors. Tie2 receptor kinase inhibitors may be used in the treatment, including prophylaxis, of inhibition of angiogenesis, or chronic inflammatory or proliferative or angiogenic diseases or disorders which are caused by excessive or inappropriate angiogenesis in a mammal in need thereof.

The novel compounds of Formula (I) are represented by the structure:

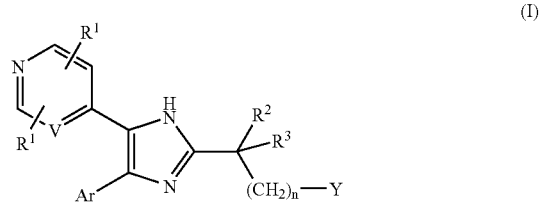

wherein

V is CH or N;

Ar is a napth-2-yl, napth-1-yl, a bicyclic or a tricyclic heteroaromatic ring, which rings may be optionally substituted;

Y is $NR^{10}R^{11}$, $NR^{10}C(Z)NR^{10}R^{11}$, $NR^{10}C(Z)NR^{10}C(Z)OR^{11}$, $NR^{10}COOR^{11}$ or $NR^{10}SO_2R^{11}$;

n is 0, 1, 2, 3 or 4;

X is O, $CH_2$, S or NH;

Z is oxygen or sulfur;

$R^1$ is independently hydrogen, $X-R^4$, halogen, hydroxy, optionally substituted $C_{1-6}$ alkyl, optionally substituted $C_{1-6}$alkylsulfinyl, $CH_2OR^5$, amino, mono or di-$C_{1-6}$alkylamino, $N(R^6)C(O)R^7$, $N(R^6)S(O)_2R^8$, or a 5 to 7-membered N-heterocyclyl ring which optionally contains an additional heteroatom selected from O, S and $NR^9$.

$R^2$ and $R^3$ independently represent optionally substituted $C_{1-6}$alkyl, or $R^2$ and $R^3$ together with the carbon atom to which they are attached form an optionally substituted $C_{3-7}$cycloalkyl or $C_{5-7}$ cycloalkenyl ring, or $R^2$ and $R^3$ together with the carbon atom to which they are attached form an optionally substituted 5 to 7-membered heterocyclyl ring containing up to 3 heteroatoms selected from N, O and S.

$R^4$ is independently $C_{1-6}$alkyl, aryl, aryl$C_{1-6}$alkyl, heterocyclyl, heterocyclyl$C_{1-6}$alkyl, heteroaryl, or a heteroaryl$C_{1-6}$ alkyl moiety, and wherein any of these moieties may be optionally substituted;

$R^5$ is hydrogen, $C(Z)R^{12}$ or optionally substituted $C_{1-6}$alkyl, optionally substituted aryl, optionally substituted aryl$C_{1-6}$alkyl, or $S(O)_2R^8$;

$R^6$ is hydrogen or $C_{1-6}$alkyl;

$R^7$ is hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl;

$R^8$ is $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl;

$R^9$ is hydrogen, $C_{1-4}$alkyl, $C_{3-7}$cycloalkyl or aryl;

$R^{10}$ and $R^{12}$ are independently selected from hydrogen, $C_{1-6}$alkyl, $C_{3-7}$cycloalkyl, $C_{3-7}$cycloalkyl $C_{1-6}$alkyl, aryl, aryl$C_{1-6}$alkyl, heterocyclyl, heterocyclyl$C_{1-6}$alkyl, heteroaryl and heteroaryl$C_{1-6}$alkyl, any of which may be optionally substituted; and $R^{11}$ is hydrogen, $C_{1-6}$alkyl, $C_{3-7}$cycloalkyl, $C_{3-7}$cycloalkyl $C_{1-6}$alkyl, aryl, aryl$C_{1-6}$alkyl, heterocyclyl, heterocyclyl$C_{1-6}$alkyl, heteroaryl, or heteroaryl$C_{1-6}$alkyl, any of which may be optionally substituted; or $R^{10}$ and $R^{11}$ together with the nitrogen may form a 5 to 7 membered ring optionally containing an additional heteroatom selected from O, S, or $NR^9$;

or a pharmaceutically acceptable salt thereof

DETAILED DESCRIPTION OF THE INVENTION

The present invention is the directed to novel compounds which can inhibit Tie2 kinase, and use of these compounds for inhibition of angiogenesis in the treatment of chronic inflammatory or proliferative or angiogenic diseases which are caused by excessive or inappropriate angiogenesis in a mammal in need thereof.

In the compounds of formula (I), V is suitably CH or N, preferably carbon.

Suitably, the pyridyl or pyrimidine ring is optionally substituted, independently, one to two times independently by $R^1$.

Suitably, $R^1$ is independently hydrogen, $X-R^4$, halogen, hydroxy, optionally substituted $C_{1-6}$ alkyl, optionally substituted $C_{1-6}$alkylsulfinyl, $CH_2OR^5$, amino, mono or di-$C_{1-6}$alkylamino, $N(R^6)C(O)R^7$, $N(R^6)S(O)_2R^8$, or a 5 to 7-membered N-heterocyclyl ring which optionally contains an additional heteroatom selected from O, S and $NR^9$. Preferably, the pyridyl or pyrimidine is substituted in the 2-position. Preferably, $R^1$ is hydrogen or $X-R^4$.

X is suitably, O, $CH_2$, S or NH. Preferably X is oxygen or nitrogen.

$R^4$ is independently $C_{1-6}$alkyl, aryl, aryl$C_{1-6}$alkyl, heterocyclyl, heterocyclyl$C_{1-6}$alkyl, heteroaryl, or a heteroaryl$C_{1-6}$ alkyl moiety, and wherein any of these moieties may be optionally substituted. Preferably $R^4$ is an optionally substituted alkyl, aryl, or arylalkyl group.

When $R^4$ is aryl, it is preferably an optionally substituted phenyl. When $R^4$ is aryl alkyl, it is preferably an optionally substituted benzyl or phenethyl.

These $R^4$ moieties may be optionally substituted one or more times, preferably 1 to 3 times, independently with halogen; $C_{1-4}$ alkyl, such as methyl, ethyl, propyl, isopropyl, or t-butyl; halosubstituted alkyl, such as $CF_3$; hydroxy; hydroxy substituted $C_{1-4}$ alkyl; $C_{1-4}$ alkoxy, such as methoxy or ethoxy; $S(O)_m$alkyl and $S(O)m$ aryl (wherein m is 0, 1, or 2); $C(O)OR^{11}$, such as $C(O)C_{1-6}$ alkyl or $C(O)OH$ moieties; $C(O)R^{11}$; $OC(O)R^8$; $O-(CH_2)s-O-$, such as in a ketal or dioxyalkylene bridge (s is a number having a value of 1 to 5); amino; mono- and di-$C_{1-6}$ alkylsubstituted amino; $N(R^{10})C(O)R^7$; $C(O)NR^{10}R^{11}$; cyano, nitro, or an N-heterocyclyl ring which ring has from 5 to 7 members and optionally contains an additional heteroatom selected from oxygen, sulfur or $NR^9$; optionally substituted aryl, such as phenyl; an optionally substituted arylalkyl, such as benzyl or phenethyl; aryloxy, such as phenoxy; or arylalkyloxy such as benzyloxy; these aryl and arylalkyl moieties may be substituted with halogen, alkyl, alkoxy, $S(O)m$ alkyl, amino, or mono- and di-$C_{1-6}$ alkylsubstituted amino.

Preferably the $R^4$ moieties are substituted with an amino, mono- or di-$C_{1-6}$ alkylsubstituted amino, or an N-heterocyclyl ring which ring has from 5 to 7 members and optionally contains an additional heteroatom selected from oxygen, sulfur or $NR^9$.

Suitably, $R^2$ and $R^3$ independently represent optionally substituted $C_{1-6}$alkyl, or $R^2$ and $R^3$ together with the carbon atom to which they are attached form an optionally substituted $C_{3-7}$cycloalkyl or $C_{5-7}$ cycloalkenyl ring, or $R^2$ and $R^3$ together with the carbon atom to which they are attached form an optionally substituted 5 to 7-membered heterocyclyl ring containing up to 3 heteroatoms selected from N, O and S. Preferably $R^2$ and $R^3$ independently represent optionally substituted $C_{1-6}$alkyl.

Suitably, n is 0, 1, 2, 3 or 4. Preferably, n is 1.

Suitably, Y is $NR^{10}R^{11}$, $NR^{10}C(Z)NR^{10}R^{11}$, $NR^{10}C(Z)NR^{10}C(Z)OR^{11}$, $NR^{10}COOR^{11}$ or $NR^{10}SO_2R^{11}$.

Suitably, $R^{11}$ is hydrogen, $C_{1-6}$alkyl, $C_{3-7}$cycloalkyl, $C_{3-7}$cycloalkyl $C_{1-6}$alkyl, aryl, aryl$C_{1-6}$alkyl, heterocyclyl, heterocyclyl$C_{1-6}$alkyl, heteroaryl, or heteroaryl$C_{1-6}$alkyl, any of which may be optionally substituted; or $R^{10}$ and $R^{11}$ together with the nitrogen to which they are attached form a 5 to 7 membered heterocyclic ring optionally containing an additional heteroatom selected from O, S, or $NR^9$.

While $R^{11}$ is optionally substituted as defined in the specification, it is preferably, an unsubstituted or substituted alkyl, $C_{3-7}$cycloalkyl, $C_{3-7}$cycloalkyl $C_{1-6}$alkyl, heterocyclyl, heterocyclyl $C_{1-6}$alkyl, heteroaryl, or a heteroaryl$C_{1-6}$ alkyl. The alkyl if substituted is preferably substituted one or more times by halogen, such as in $CF_3$, $CH_2CF_3$, or $(CH_2)_2Cl$ or $(CH_2)_3Cl$, or by a $C_{1-6}$alkoxy, a $C_{1-6}$alkylthio, $C_{1-6}$alkyl sulphinyl or $C_{1-6}$alkyl sulphonyl group; if $R^{11}$ is a $C_{3-7}$cycloalkyl $C_{1-6}$alkyl, it is preferably a 5 or 6 membered ring, such as cyclohexylmethyl; if $R^{11}$ is a heterocyclyl $C_{1-6}$alkyl, it is preferably a morpholino $C_{1-6}$alkyl, or a piperidine $C_{1-6}$alkyl; or if a heteroaryl$C_{1-6}$alkyl moiety, an optionally substituted isoxazolyl.

Suitably, $R^{10}$ and $R^{12}$ are independently selected from hydrogen, $C_{1-6}$alkyl, $C_{3-7}$cycloalkyl, $C_{3-7}$cycloalkyl $C_{1-6}$alkyl, heterocyclyl, heterocyclyl$C_{1-6}$alkyl, aryl, aryl$C_{1-6}$alkyl, heteroaryl or heteroaryl$C_{1-6}$alkyl, any of which may be optionally substituted. The $R^{10}$ group and $R^{12}$ moieties may be optionally substituted as defined for the alkyl term.

Suitably, $R^5$ is hydrogen, $C(Z)R^{12}$ or optionally substituted $C_{1-6}$alkyl, optionally substituted aryl, optionally substituted aryl$C_{1-6}$alkyl, or $S(O)_2R^8$.

Suitably, $R^6$ is hydrogen or $C_{1-6}$alkyl.

Suitably, $R^7$ is hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl.

Suitably, $R^8$ is $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl.

Suitably, $R^9$ is hydrogen, $C_{1-4}$alkyl, $C_{3-7}$cycloalkyl or aryl.

Suitably, $R^{10}$ and $R^{12}$ are independently selected from hydrogen, $C_{1-6}$alkyl, $C_{3-7}$cycloalkyl, heterocyclyl, heterocyclyl$C_{1-6}$alkyl, aryl, aryl$C_{1-6}$alkyl, heteroaryl or heteroaryl$C_{1-6}$alkyl, any of which may be optionally substituted.

Suitably, Z is oxygen or sulfur.

Suitably, Ar is a napth-2-yl, napth-1-yl, a bicyclic or a tricyclic heteroaromatic ring, which ring, may be optionally substituted in any ring. A bicyclic or tricyclic heteroaromatic ring system is a fused ring system that may include a carbocyclic ring. Examples of such ring, systems include quinoline, isoquinoline, benzimidazole, benzothiophene or benzofuran, benzoxazole, benzthiazole, dibenzofuran, dibenzothiophene, benzthiodiazole, benztriazole, or indolyl.

The Ar ring may be optionally substituted one or more times, preferably 1 to 3 times, independently, in any ring. Suitable substituents include halogen, $C_{1-6}$alkyl, aryl, aryl$C_{1-6}$alkyl, cycloalkyl, cycloalkyl $C_{1-6}$alkyl, $C_{1-6}$alkoxy$C_{1-6}$alkyl, halosubstituted $C_{1-6}$alkyl, aryl$C_{1-6}$alkoxy, $(CR^{13}R^{14})_tOR^{12}$, nitro, cyano, $(CR^{13}R^{14})_tNR^{10}R^{11}$, $(CR^{13}R^{14})_tNR^{10}C(Z)R^{12}$, $(CR^{13}R^{14})_tC(Z)NR^{10}R^{11}$, $(CR^{13}R^{14})_tCOR^{12}$, $(CR^{13}R^{14})_tZC(Z)R^{12}$, $(CR^{13}R^{14})_tC(Z)OR^{12}$, $(CR^{13}R^{14})_tC(O)NR^{10}R^{11}$, $(CR^{13}R^{14})_tNR^{10}C(Z)NR^{10}R^{11}$, $(CR^{13}R^{14})_tNR^{10}C(=NH)NR^{10}R^{11}$, $(CR^{13}R^{14})_tC(=NH)-NR^{10}R^{11}$, $(CR^{13}R^{14})_tNR^{10}S(O)_2R^8$, $(CR^{13}R^{14})_tS(O)_2NR^{10}R^{11}$, $(CR^{13}R^{14})_tS(O)_mR^{12}$, heterocyclyl, heteroaryl, heterocyclyl$C_{1-6}$alkyl or heteroaryl $C_{1-6}$alkyl.

Suitably t is 0, or an integer having a value of 1 to 10. Preferably t is 0, or 1, more preferably 0.

Suitably, $R^{13}$ and $R^{14}$ are independently hydrogen, or a $C_{1-6}$ alkyl.

Preferably, Ar is substituted one or more times by halo, cyano, $(CR^{13}R^{14})_tC(Z)NR^{10}R^{11}$, $(CR^{13}R^{14})_tC(Z)OR^{12}$, $(CR^{13}R^{14})_tCOR^{12}$, $(CR^{13}R^{14})_tS(O)_mR^{12}$, $(CR^{13}R^{14})_tOR^{12}$, halo-substituted-$C_{1-6}$ alkyl, $C_{1-6}$ alkyl, $(CR^{13}R^{14})_tNR^{10}C(Z)R^{12}$, $(CR^{13}R^{14})_tNR^{10}S(O)_2R^8$, $(CR^{13}R^{14})_tS(O)_2NR^{10}R^{11}$, $(CR^{13}R^{14})_tZC(Z)R^{12}$, or $(CR^{13}R^{14})_tNR^{10}R^{11}$.

Preferably, the Ar ring is substituted one or more times by halo, hydroxy, $C_{1-6}$alkyl, halosubstituted $C_{1-6}$alkyl, hydroxy $C_{1-6}$alkyl, and $C_{1-6}$alkoxy. More preferred substitution is $C_{1-6}$alkoxy group, such as methoxy; a $C_{1-6}$ alkyl, such as methyl, or halogen, such as fluorine or chlorine.

Preferably the Ar ring is a naphthyl ring, more preferably a napth-2-yl ring. If Ar is a bicycloheteroaryl ring it is preferably a benzothiophene or a benzofuran ring. A preferred ring placement for the napth-2-yl ring is in the 6-position.

For use herein, the term "alkyl", and "alkenyl" groups, individually or as part of a larger group e.g. "alkoxy", may be straight or branched chain radicals containing up to six carbon atoms, unless otherwise limited, including, but not limited to, methyl, ethyl, n-propyl, iso-propyl, n-butyl, sec-butyl, iso-butyl, tert-butyl, and the like. The alkyl and alkenyl groups may be optionally substituted as herein defined.

For use herein, "cycloalkyl" includes cyclic radicals having from three to eight ring carbon atoms, including but not limited to cyclopropyl, cyclopentyl, cyclohexyl, and the like. The cycloalkyl groups may be optionally substituted as herein defined.

For use herein, "cycloalkenyl" includes cyclic radicals, preferably of 5 to 8 carbons, which have at least one bond including but not limited to cyclopentenyl, cyclohexenyl, and the like. The cycloalkenyl groups may be optionally substituted as herein defined.

For use herein the term "aryl" (on its own or in any combination, such as "arylalkyl" or "aryloxy") includes a single or fused ring system, suitably containing from 4 to 7, preferably 5 or 6 ring atoms in each ring, which rings, may each be unsubstituted or substituted by, independently for example, up to three substituents. A fused ring system may include an aliphatic ring, such as a saturated or partially saturated ring, and need include only one aromatic ring. Suitable aryl groups include phenyl and naphthyl such as 1-naphthyl or 2-naphthyl. The aryl rings may be optionally substituted as herein defined unless otherwise indicated.

For use herein the term "heterocyclyl" (on its own or in any combination, such as "heterocyclyl alkyl" or "heterocyclyl oxy") suitably includes, unless otherwise defined, non-aromatic, single and fused rings suitably containing up to four heteroatoms in each ring, each of which independently selected from O, N and S, and which rings, may be unsubstituted or substituted independently by, for example, up to three substituents. Each heterocyclic ring suitably has from 4 to 7, preferably 5 or 6, ring atoms. A fused heterocyclic ring system may include carbocyclic rings and need include only one heterocyclic ring. Examples of heterocyclyl groups include pyrrolidine, piperidine, piperazine, morpholine, imidazolidine and pyrazolidine. The heterocyclic and heterocyclic rings may be optionally substituted as herein defined, unless otherwise indicated.

When used herein, the term "heteroaryl" (on its own or in any combination, such as "heteroaryloxy" or "heteroarylalkyl") suitably includes, unless otherwise defined, mono- and bicyclic heteroaromatic ring systems comprising up to four, preferably 1 or 2, heteroatoms each selected from O, N and S. Each ring may have from 4 to 7, preferably 5 or 6, ring atoms. A bicyclic heteroaromatic ring system may include a carbocyclic ring. Examples of heteroaryl groups include pyrrole, quinoline, isoquinoline, pyridine, pyrimidine, oxazole, thiazole, thiadiazole, triazole, imidazole, benzimidazole, isoxazole, thiophene, benzothiophene, furan and benzofuran. The heteroaryl rings may be optionally substituted as defined herein unless otherwise indicated.

Suitably the when the term "optionally substituted" is used herein, such as on the alkyl, alkenyl, cycloalkyl, cycloalkenyl, aryl, arylalkyl, heterocyclyl, heterocyclicalkyl, heteroaryl, and heteroarylalkyl groups, unless otherwise defined, shall mean that the group may be optionally substituted one or more times, preferably by one to three substituents, each independently selected from halogen, $C_{1-6}$alkyl, aryl, aryl$C_{1-6}$alkyl, cycloalkyl, cycloalkyl $C_{1-6}$alkyl, $C_{1-6}$alkoxy$C_{1-6}$alkyl, halosubstituted $C_{1-6}$alkyl, aryl$C_{1-6}$alkoxy, $(CR^{13}R^{14})_tOR^{12}$, nitro, cyano, $(CR^{13}R^{14})_tNR^{10}R^{11}$, $(CR^{13}R^{14})_tNR^{10}C(Z)R^{12}$, $(CR^{13}R^{14})_tC(Z)NR^{10}R^{11}$, $(CR^{13}R^{14})_tCOR^{12}$, $(CR^{13}R^{14})_tZC(Z)R^{12}$, $(CR^{13}R^{14})_tC(Z)OR^{12}$, $(CR^{13}R^{14})_tC(O)NR^{10}R^{11}$, $(CR^{13}R^{14})_tNR^{10}C(Z)NR^{10}R^{11}$, $(CR^{13}R^{14})_tNR^{10}C(=NH)NR^{10}R^{11}$, $(CR^{13}R^{14})_tC(=NH)-NR^{10}R^{11}$, $(CR^{13}R^{14})_tNR^{10}S(O)_2R^8$, $(CR^{13}R^{14})_tS(O)_2NR^{10}R^{11}$, $S(O)_mR^{12}$, heterocyclyl, heteroaryl, heterocyclylC$_{1-6}$alkyl or heteroaryl C$_{1-6}$alkyl. In addition, two adjacent ring carbon atoms may be linked to form a bicyclic system.

Particular compounds according to the invention include those mentioned in the examples and their pharmaceutically acceptable salts.

It will be appreciated that for use in medicine the salts of the compounds of formula (I) should be pharmaceutically acceptable. Suitable pharmaceutically acceptable salts will be apparent to those skilled in the art and include those described in *J. Pharm. Sci.,* 1977, 66, 1–19, such as acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amounts of water.

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Compounds of formula (I) are imidazole derivatives which may be readily prepared using procedures well-known to those skilled in the art, and described in, for instance, Comprehensive Heterocyclic Chemistry, Editors Katritzky and Rees, Pergamon Press, 1984, 5, 457–497, from starting materials which are either commercially available or can be prepared from such by analogy with well-known processes. A key step in many such syntheses is the formation of the central imidazole nucleus, to give compounds of formula (I). These patents describe the synthesis of α-ketooximes and α-hydroxyketones (benzoins) and their subsequent use in preparing imidazoles and N-hydroxyl imidazoles. Thereafter, further compounds of formula (I) may be obtained by manipulating substituents in any of the groups HetAr, Ar and Y$_1$ using conventional functional group interconversion procedures.

In particular, in a first process, compounds of formula (I) may be prepared by condensing an alpha-diketone of formula (II):

(II)

wherein Ar is defined for formula (I), or an equivalent thereof and HetAr is defined as the

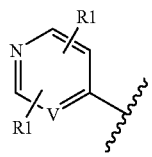

fragment of Formula I, (it should be noted that in the schemes below R$^1$ is shown as X—R$^4$ for representative purposes only), with an aldehyde of the formula (III):

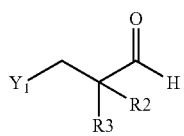
(III)

wherein Y$_1$ is a group convertible to Y, and R$^2$ and R$^3$ is as hereinbefore defined, or an equivalent thereof, and, if necessary, with ammonia or a source thereof, under imidazole-ring forming conditions.

The croup Y$_1$, as used in these schemes, is a group convertible to Y. The conversions to Y$_1$ are well known to the skilled artisan using readily available techniques. For instance, Y$_1$ could be a protected amine, such as CBZ or and S-BOC amine, which is deprotected and converted to Y; alternatively Y$_1$ could be a carboxylic acid or a carboxylic acid ester, which can be converted by well known means to an amine, a bromide or an azide (i.e. a 1 carbon degradation) and further functionalized; alternatively Y$_1$ could be a protected alcohol, and using standard functional group interconversion converted to an amine, such as azide and reduced. etc. to the group Y.

Suitable equivalents of the alpha-diketone are well known to those skilled in the art and include the corresponding alpha-keto-oxime and alpha-dioxime. Suitable equivalents of the aldehyde of formula (III) are well known in the art and include the corresponding oxime and acetal.

Ammonia, or a source thereof, is preferably used in excess, with at least a dimolar amount being used in the case of the alpha-diketone and at least an equimolar amount in the case of the alpha-keto-oxime.

Suitable sources of ammonia include ammonium salts of organic carboxylic acids, such as ammonium trifluoroacetate or an ammonium C$_{1-6}$ alkanoate, for instance ammonium acetate and ammonium formate, preferably ammonium acetate, and carboxylic amides, in particular of formic acid, such as formamide. An ammonium salt is generally used in large excess and in the presence of an acid, such as a C$_{1-6}$ carboxylic acid which acid may also be used as a solvent for the reaction. If formamide is used, this may be used in excess, as the reaction solvent. An alternative solvent such as ethanol or dimethyl sulphoxide (Lantos et al, *J Het Chem,* 19, 1375, 1982) may be used. An additional solvent may also be employed, for instance, dimethyl formamide may be used with formamide. The reaction is generally carried out at elevated temperatures, for instance under reflux conditions, and if desired, in a sealed vessel optionally under pressure and/or an inert gas atmosphere, for instance nitrogen. It is also possible to run the reaction at elevated temperature in a molten salt, which contains a source of ammonia, for example in ammonium trifluoroacetate.

A further suitable source of ammonia is hydroxylamine, in which case the initially formed imidazole is an N-hydroxy-N-oxide imidazole. This may then be reduced to the corresponding N-hydroxy imidazole by treating with a suitable reducing agent such as sodium borohydride, in an appropriate solvent such as methanol, following the method of Akange and Allan, Chem and Ind, 5 Jan. 1975, 38. The N-hydroxy imidazole may in turn be converted to an imidazole of formula (I) by treatment with a conventional deoxygenating agent such as titanium trichloride, phosphorus trichloride or a trialkylphosphite such as trimethyl- or triethyl-phosphite. N-hydroxy-N-oxide imidazoles may be readily obtained by treating an alpha-diketone of formula (II) with an aldehyde of formula (III) with about two equivalents of hydroxylamine or the corresponding aldoxime and about one equivalent of hydroxylamine, under proton catalysis. Alternatively, the N-oxide may be obtained by the acid catalyzed condensation of the corresponding alpha-dioxime or alpha-keto-oxime with an aldoxime of the aldehyde of formula (III).

When the compound of formula (II) above is an alpha-keto-oxime derivative, it will be appreciated that the product initially obtained will be a compound of formula (I) in which the imidazole is N-hydroxylated and which may be converted into a compound of formula (I) as described above.

It will be appreciated by those skilled in the art that in some instances, it will not be necessary to provide a separate source of ammonia as the alpha-diketone or aldehyde equivalent may already contain such a source. Examples of this include alpha-dioxime or alpha-keto-oxime and aldoxime.

Preferred methods for preparing compounds of this invention are as outlined in the Schemes I–III.

In Scheme I, the anion prepared from 1 (a specific example being V=CH, X=S, $R_1$=Me), by treatment with a strong base such as lithium di-iso-propylamide, is condensed with an aryl aldehyde, to give, after removal of the protecting group, the diol 2. This may then be converted to the alpha-diketone 3 by a Swern oxidation of which any number of potentially useful variations are known and may be used. The alpha-diketone 3 is then cyclised to an imidazole 4 by heating 3 with a substituted aldehyde of formula (III) in a mixture of ammonium acetate, as the source of ammonia, and an appropriate solvent, for example acetic acid or DMSO. The imidazole 4, with the group $Y_1$ may be converted into a group Y using conventional functional group interconversion procedures to afford imidazole 5, a compound of formula I. Functional group transformations are well known in the art and are described in, for instance, *Comprehensive Organic Functional Group Transformations*, eds. A. R. Katritzky, O. Meth-Cohn, and C. W. Rees (Elsevier Science Ltd., Oxford, 1995), *Comprehensive Organic Chemistry*, eds. D. Barton and W. D. Ollis (Pergamon Press, Oxford, 1979), and *Comprehensive Organic Transformations*, R. C. Larock (VCH Publishers Inc., New York, 1989). An example of a preferred $Y_1$ group is $CH_2NH_2$ or a protected form thereof e.g. $CH_2NHBoc$. Scheme I also illustrates the preparation of a protected alpha-hydroxyketone 6, by condensing the anion of 1 with an appropriately activated carbonyl derivative of a substituted benzamide, such as the N-methoxy-N-methylamide, to yield a protected a-hydroxyketone. This adduct 6 may then be directly converted to the imidazole 4, using a combination of a copper (II) salt, such as copper (II) acetate, as an oxidizing agent and ammonium acetate as a source of ammonia. The alpha-hydroxyketone 6 may also be deprotected and then oxidized to give an alpha-diketone 3, for instance using Swern oxidation.

Scheme I

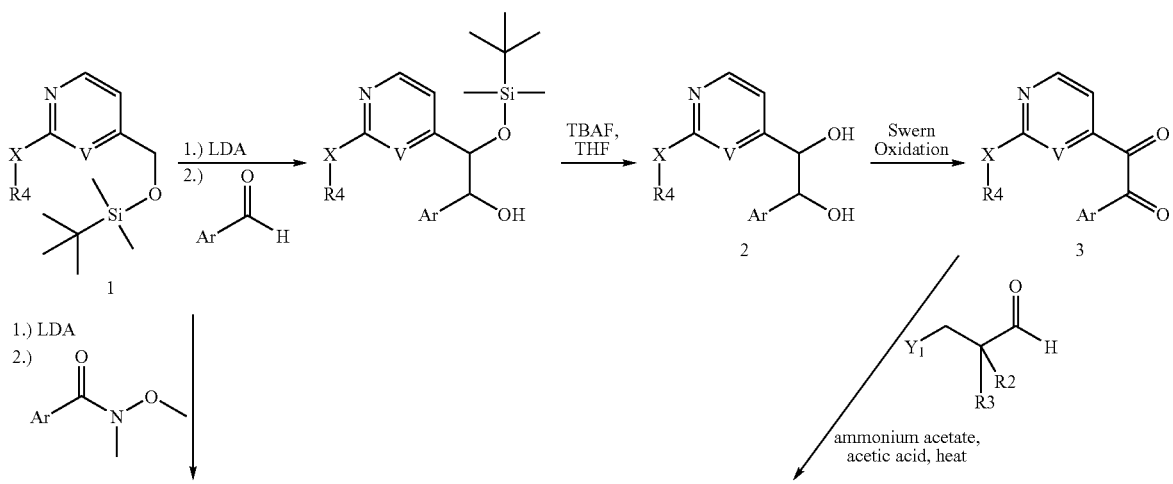

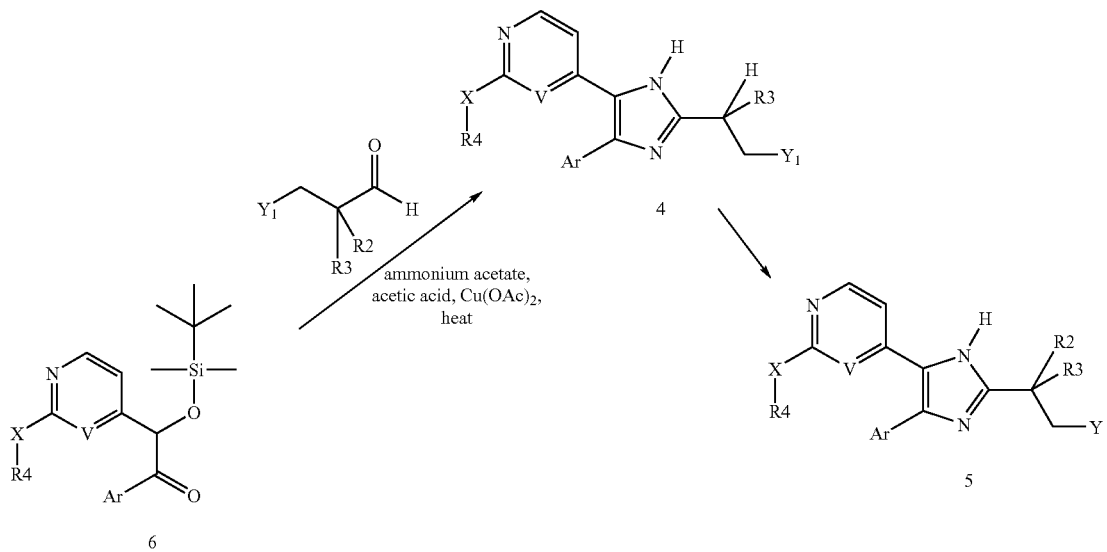

X = O, S, NH
V = CH, N

Scheme II illustrates the use of an alpha-keto-oxime for preparing a compound of formula (I). A heterocyclic ketone 7 (for example, V=N, X=S, R₁=Me) is prepared by adding the anion of 2-methylthio-6-methylpyrimidine (prepared by treatment thereof with an alkyl lithium, such as n-butyl lithium) to an N-alkyl-O-alkoxybenzamide. Alternatively, the anion may be condensed with a benzaldehyde, to give an alcohol that is then oxidized to the ketone 7. The alpha-keto-oxime 8 is then prepared from 7 using standard conditions, such as reaction with sodium nitrite, and this may then be reacted with an aldehyde of formula (III) to afford an N-hydroxyimidazole 9. This may converted to 10, by treating it with a deoxygenating agent such as titanium trichloride, phosphorus trichloride or a trialkyl phosphite, such as trimethyl or triethylphosphite. Functional group interconversion then may be employed to convert Y₁ of 10 to afford 11, a compound of formula (I) with Y as hereinbefore defined. Furthermore, oxidation of the sulfur (X=S) of 5 or 11 to the sulfoxide or sulfone followed by nucleophilic displacement with oxygen, nitrogen or sulfur nucleophiles affords compounds of Formula I (X=O, N, or S; compounds 5 and 11 in Schemes I and II).

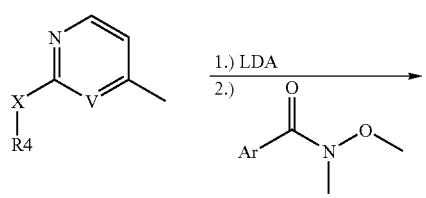

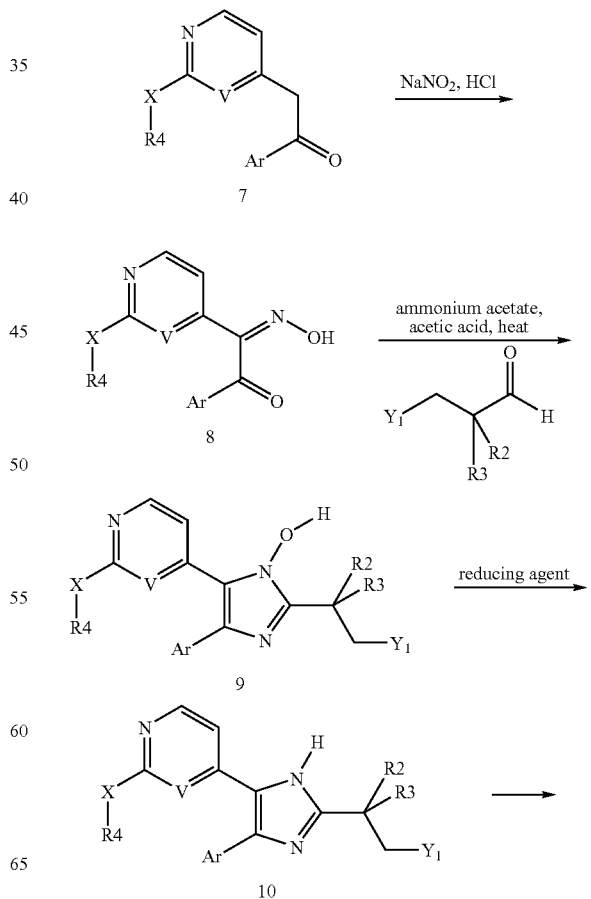

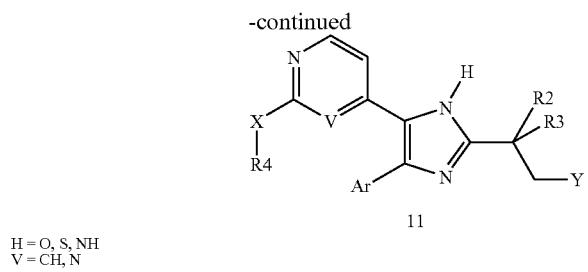

H = O, S, NH
V = CH, N

Compounds of the general formula (V═CH, X═O, N, S) can be prepared as in Schemes I or II except substituting 4-methyl-2-chloropyridine or 4-methyl-2-fluoropyridine for the starting 2-methylthio-6-methylpyrimidine or pyridine (1) (Gallagher et al *Bioorg. Med. Chem.* 5, 49, 1997). Nucleophilic substitution of the resulting 2-halopyridinylimidazole can be effected by the procedure described in U.S. Pat. No. 5,670,527. Alternatively, oxidation of the sulfur (X═S) to the sulfoxide or sulfone followed by nucleophilic displacement with oxygen, nitrogen or sulfur nucleophiles affords compounds of Formula I (compounds 5 and 11 in Schemes I and II).

Alternatively compounds may be prepared as in Scheme III wherein the Ar group is added last. (X, $R^2$, $R^3$, and Y are as defined for formula (I), and $Y_1$ is a group convertible to Y).

Scheme III

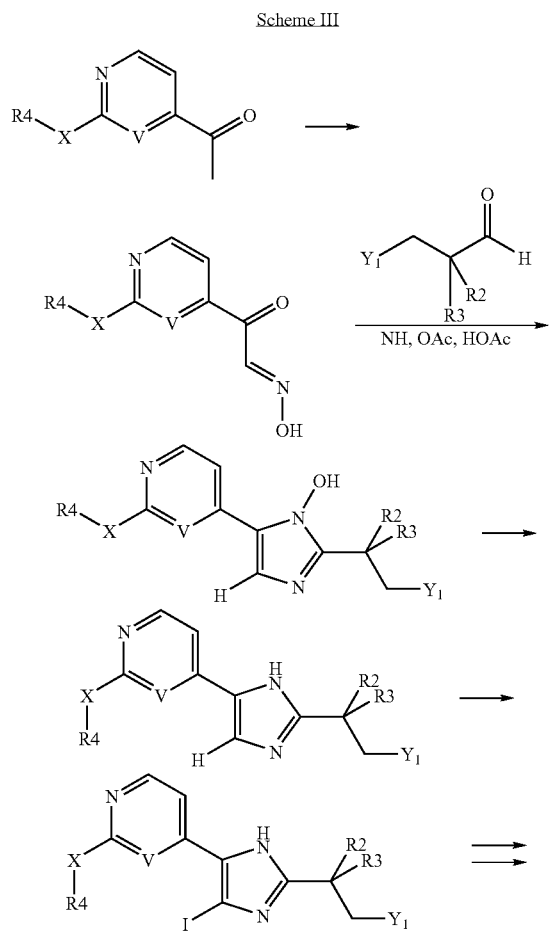

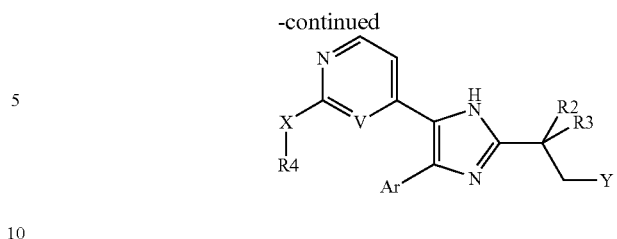

Oxidation of a 4-acetyl substituted pyridine derivative (V═CH, X═S, $R_1$═Me) with sodium nitrite affords the ketooxime. Heating this product with an alkyl aldehyde and ammonium acetate in acetic acid allows access to the imidazole nucleus. Reduction of the hydroxyimidazole may be accomplished with heating with a trialkyl phosphite or stirring at ambient temperature with titanium trichloride. Treatment of the imidazole with N-iodosuccinimide gives the iodoimidazole with then may be reacted with various boronic acids under palladium catalysis to give the aryl or heteroaryl imidazoles. Alternative biaryl coupling reactions may also be used.

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Pharmaceutically acceptable salts may be prepared conventionally by reaction with the appropriate acid or acid derivative.

Methods of Treatment

The Tie receptors are proteins of approximately 125 kDa, with a single putative transmembrane region. The extracellular domain of these receptors is divided into several regions: there are 3 regions that have a pattern of cysteine expression found in EGF-like domains; there are 2 regions that have some weak homology to and structural characteristics of immunoglobulin-like domains; and there are 3 regions with homology to the fibronectin III repeat structure. This particular combination of extracellular domains is unique to the Tie receptors. The intracellular portion of Tie2 is most closely related (~40% identity) to the kinase domains of FGF-R1, PDGF-R and c-kit. The intracellular portions of Tie2 contain all of the features of tyrosine kinases, including a GXGXXG ATP binding site consensus sequence and typical tyrosine kinase motifs (i.e., HRD-LAARN and DFGL).

These receptors have sparked interest because they are the only receptor tyrosine kinases, other than those receptors for vascular endothelial cell growth factor (VEGF), that are largely restricted to endothelial cells in their expression. There are several lines of evidence showing that Tie2 is important in angiogenesis, detailed in the following paragraphs.

a. Tie1 and Tie2 Receptor location i. Embryological Vascular Development

The location of the Tie receptors in the embryo has been studied by a number of investigators using in situ hybridization. Korhonen et al. (*Blood* 80:2548–2555, 1992) showed that the mRNA for Tie receptors is located in endothelial cells of all forming blood vessels and in the endocardium of mouse embryos. During embryonic development, expression of the Tie receptors is seen in angioblasts and all developing vasculature. Expression of the Tie receptors follows expression of the major VEGF receptor, Flk-1, by 12–24 hours during mouse embryogenesis, perhaps suggesting sequential and different actions of these receptor systems (Schnurch and Risau, *Development* 119: 957–968, 1993). Cloning of a 1.2 Kb genomic 5' flanking region of Tie2, coupled to a lacZ gene and expressed in transgenic mice, demonstrated a selective pattern of expression in endothelial cells during embryonic development (Schlaeger et al., *Development* 121:1089–1098, 1995). Thus, the Tie2 promoter acts to assure endothelial cell-specific expression of Tie2.

ii. In Adult Tissues

The similarities between embryonic angiogenesis and pathologic angiogenesis yields the hypothesis that blocking Tie2 function, in tumors or chronic inflammatory settings, for examples, may block angiogenesis, thus blocking further cell proliferation and provide therapeutic benefit. Tie mRNA cannot be observed in adult skin, except at sites of active wound healing, where the proliferating capillaries in the granulation tissue contain abundant Tie mRNA (Korhonen et al., *Blood* 80:2548–2555, 1992). PCR amplification of cDNA from normal skin fails to show a signal for Tie receptor (Kaipainen et al., *Cancer Res.* 54:6571–6577, 1994). In contrast, a strong signal is seen with cDNA from metastasizing melanomas, where in situ studies localize this signal to the vascular endothelium. While Tie receptor expression is down-regulated in the established vasculature, it is upregulated in the angiogenesis that occurs in the ovary during ovulation, in wounds and in tumor (breast, melanoma and renal cell carcinoma) vasculature, consistent with prevailing views that angiogenesis in the adult borrows from embryonic angiogenic mechanisms.

b. Tie Knockout Animals

Homozygous mice with a Tie2 knockout, or carrying a transgene encoding a "dominant-negative" Tie2 receptor, confirmed that the Tie2 receptor is critical for embryonic development (Dumont et al., *Genes Dev.* 8: 1897–1909, 1994; Sato et al., *Nature* 376:70–74, 1995). Embryonic death in these mice occurred due to vascular insufficiency and there were dramatically reduced numbers of endothelial cells. Vasculogenesis—that is the differentiation of endothelial cells and the in situ formation of vessels—appeared relatively normal in mice lacking Tie2. The subsequent sprouting and remodelling resulting in formation of vessel branches (angiogenesis) was drastically reduced in the Tie2 mutant mice embryos. This lack of sprouting and angiogenesis resulted in substantial growth retardation, particularly of the brain, neural tube and heart, resulting in lack of viability. This exemplifies the critical importance of Tie2 in angiogenesis. This is significant, as angiogenesis is regulated by a number of growth factors. Interestingly, Flk1 (VEGF receptor) knockout mice exhibit embryo lethal defects in vasculogenesis that occur earlier than those of Tie2 disruption. Disruption of the Tie 1 receptor yields a much different, and later, defective phenotype; the motise embryo dies late in development due to haemorrhage resulting from defective integrity of an otherwise well formed vasculature. Taken together, these studies suggest that the VEGF/Flk1 and Tie systems operate in sequential fashion, with Tie2 having a critical role in angiogenesis.

c. Tie2 Ligands

Recently, two ligands for the Tie2 receptor have been reported. Angiopoietin-1 binds and induces the tyrosine phosphorylation of Tie2 and its expression in vivo is in close proximity with developing blood vessels (Davis et al., *Cell* 87:1161–1169, 1996). Mice engineered to lack Angiopoietin-1 display angiogenic deficits reminiscent of those previously seen in mice lacking Tie2 receptors, demonstrating that Angiopoietin-1 is a primary physiologic ligand for Tie2 and that Tie2 has critical in vivo angiogenic actions (Suri et al., *Cell* 87:1171–1180, 1996). Angiopoietin-2 was identified by homology screening and shown to be a naturally occurring antagonist for Tie2 receptors. Transgenic overexpression of Angiopoietin-2 disrupts blood vessel formation in the mouse embryo (Maisonpierre et al., *Science* 277: 55–60, 1997). Together, these results support a role for Tie2 receptors in angiogenesis.

In order to use the compounds of formula (I) in therapy, they will normally be formulated into a pharmaceutical composition in accordance with standard pharmaceutical practice.

According to a further aspect of the invention there is provided a pharmaceutical composition comprising a compound of formula (I) or a pharmaceutically acceptable salt thereof and a pharmaceutically acceptable carrier.

No toxicological effects are indicated/expected when a compound of formula (I) is administered in the above mentioned dosage range.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers is lactose, terra alba, sucrose, talc, gelatin, agar, pectin, acacia, magnesium stearate, stearic acid and the like. Exemplary of liquid carriers is syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably include a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

The compounds of Formula (I) may also be used topically in the treatment or prophylaxis of disease states exacerbated by excessive or inappropriate angiogenesis.

The compounds of Formula (I) are administered in an amount sufficient to inhibit Tie2 receptor activity such that it is regulated down to normal levels, or in some case to subnormal levels, so as to ameliorate or prevent the disease state.

Chronic diseases which have an inappropriate angiogenic component are various ocular neovasularizations, such as diabetic retinopathy and macular degeneration.

Other chronic diseases which have an excessive or increased proliferation of vasculature are tumor growth and metastasis, athrosclerosis, and certain arthritic conditions. Therefore Tie2 tyrosine kinase receptor inhibitors will be of utility in the blocking of the angiogenic component of these disease states.

The term "excessive or increased proliferation of vasculature inappropriate angiogenesis" as used herein includes, but not limited to, diseases which are characterized by hemangiomas and ocular diseases. The term "inappropriate angiogenesis" as used herein includes, but not limited to, diseases which are characterized by vessel proliferation with accompanying tissue proliferation, such as occurs in cancer, metastasis, arthritis, psoriasis and atherosclerosis.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen will be from about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a as defined number of days, can be ascertained by those skilled in the art using conventional course of treatment determination tests.

Pharmacological Test Methods

A. Measurement of Tie2 Kinase Activity

A partial cDNA clone for the Tie2 receptor was used to make protein for Tie kinase studies. In order to generate the primary screening assay, a baculovirus expressed GST fusion for Tie2 kinase domain was constructed and expressed using the commercial vector pAcG I (Pharmingen).

This final construct was transfected into Baculovirus and soluble GST fusion products used in the screening assay. Prior work had demonstrated the use of a baculovirus expressed GST fusion for the murine Tie2 kinase domain to screen for candidate target/signaling molecules (Huang et al., Oncogene 11:2097–2103, 1995).

Tie2 kinase activity assay: The Tie2 kinase activity assay was typically run in one of 2 ways described as follows. Minor variations in the assay give similar results.

1. Autophosphorylation flashplate assay

Materials:

Kinase buffer (final 20 mM Tris-HCl, pH7.0, 100 mM NaCl, 12 mM $MgCl_2$, 1 mM DTT).

Gamma $^{33}$p-ATP (usually final amount of 0.5–1 uCi/well)

ATP (final 30 uM, or other desired concentration)

Flashplate (96-well, polystyrene microplate with plastic scintillator coated wells)

TopCount (microplate scintillation counter)

Procedures:

Turn on incubator shaker and adjust temperature to 30° C.

Add 20 ul of 3× kinase buffer per well to the Flashplate

Add 20 ul of protein per well except for background. Compounds added, typically in DMSO stocks, at 1–2 ul.

Add 20 ul mixture of gamma $^{33}$p-ATP and cold ATP per well.

Total volume is 60 ul.

Cover with transparent polyester film.

Incubate at 30° C. for two hours in shaker, or desired time.

Take Flashplate out of the shaker, wash five times (for example, with 300 ul of 10 uM ATP in 1×PBS per well).

Read plate on TopCount or other counting instrument. Results are calculated as % inhibition and IC50, using normal calculation methods.

Representative compounds of Formula (I), Example I was found to be active in the assay, having an IC50 of <1 uM.

2. Fluorescence Polarization for Tie 2 Kinase

Final Assay conditions:
  50 mM HEPES pH 7.5
  2% DMSO (when screening compounds)
  250 uM ATP
  2 mM $MgCl_2$
  1 mM DTT
  50 uM NaVanidate
  10 uM peptide substrate
  activated tie 2 kinase * see activation protocol below Peptide Substrate:
  RFWKYEFWR—OH
  MW (TFA salt)=1873 Da
  Make a 1 mM peptide stock and store at −20° C.
  Dilute to 100 uM just prior to use.

9× Kinase buffer:
  450 mM HEPES pH 7.5
  900 mM NaCl
  450 uM NaVanidate
  18 mM $MgCl_2$
  100 mM DTT
  Can be made up ahead of time and stored in aliquots at −20° C.

ATP stock:
  Make a 25 mM ATP stock and store in aliquots at −20° C. until needed.
  Dilute to 2.5 mM prior to use.

Procedure:
  For a 50 ul reaction add the following to each well of a 96-well black half-area plate (Costar, cat# 3694)
  1.5 ul of compound in 20% DMSO
  5 ul 9× kinase buffer.
  5 ul 2.5 mM ATP.
  5 ul 100 uM peptide substrate.
  25 ul PTK detection mix (Panvera, P-2652, 50 ml—UK distributor is Cambridge Bioscience)
  5 ul activated tie 2 kinase (protocol below) diluted in 1× buffer to initiate the reaction.
  7. Read polarization on an FP instrument cycling for 30–50 minutes in accordance with enzyme activity.

Representative compounds of Formula (I), Example 1 was found to be active in this fluorescence assay, having an IC50 of <1 uM.

Activation of Tie 2 Kinase Protocol:

Final Buffer Conditions:
  20 mM Tris-HCl pH 7.5
  12 mM $MgCl_2$
  100 mM NaCl
  20 uM NaVanidate
  1 mM DTT
  300 uM ATP Procedure
1. Incubate 5 uM tie 2 kinase in the 300 uM ATP and the buffering conditions described above.
2. Allow to incubate at 27° C. for 2 hours.
3. Add 2.5 ml reaction to a NAP-25 desalting column (Pharmacia Biotech cat. no. 17-0852-02) pre-equilibrated in 20 mM Tris-HCl pH 7.5, 100 mM $NaCl_2$ to separate the ATP from the enzyme.
4. Elute the enzyme with 5.0 ml 20 mM Tris-HCl pH 7.5, 100 mM $NaCl_2$; the protein concentration should be 2.5 uM at this point.
5. Aliquot out the enzyme and store at −80° C. as soon as possible.

B. Measurement of Tie2 Receptor Signal Transduction—a Cellular Assay

HEL cells (ATCC # TIB 180) are cultured at between 1 and 5×10$^5$ ml in RPMI-1640 medium supplemented with 2 mM glutamine and 10% FBS as a suspension culture. Sixteen to thirty-six hours prior to an experiment, the necessary number of cells are passaged into 0.5% FBS/RPMI medium. On the day of an experiment, cells are harvested and resuspended at a density of 0.5–1.0×10$^7$ cells ml in 0.5% FBS RPMI and seeded at 2–3 ml/well in six well plates.

Alternatively, Human Umbilical Vein Endothelial Cells (HUVECs) (Clonetics—Walkersville, Md.) may be used for the assay. HUVECs between passages 2 and 12, are plated at 2×10$^5$ and 1×10$^6$ cells per well in a six well plate in supplemented EGM (Clonetics). After 24 hours the media is changed to EBM containing 3% BSA (Clonetics), and the cells are cultured overnight and used for assay the following day.

Cells are treated with inhibitory compounds at appropriate concentrations for 30–45 minutes. The contents of the wells are mixed briefly on a rocker (approx. 30 seconds) and then incubated at 37° C. The cells are then treated with a source of native ligand, such as serum or fibroblast conditioned medium for 10 minutes At the end of 10 minute incubation period the plate is placed on ice. The cells are harvested and the media is removed. The cells are lysed in denaturing sample buffer (Invitrogen—Carlsbad, Calif.). The suspension is sonicated for 5 pulses at a medium setting and returned to ice. The phosphorylation state of the Tie2 receptor is determined Western blotting-and detection by an anti-phospho-Tie2 antibody, as detailed below (Harlow, E., and Lane, D. P., *Antibodies—A Laboratory Manual*, Cold Spring Harbor Laboratory Press: New York, 1988.). Thirty ul of the lysate are run on a 7.5% SDS/polyacrylamide gel. The gel is then transferred to a nitrocellulose or PVDF membrane as per the manufacturer's instructions for Western blotting.

The blots are washed with PBS 0.05% between –20 and then blocked with 3% BSA/PBS/Tween for 1 hour at room temperature. The blots are then incubated with 1 ug/ml anti-phospho-Tie2 antibody (SmithKline Beecham) in PBS/ 0.05% Tween for 1 hour. The blot is then washed 4 times with PBS/Tween for 5 minutes each. The blot is incubated with an anti-mouse-HRP conjugate secondary antibody at the dilution recommended by the manufacturer, in PBS/ Tween for 1 hour. The blot is washed in PBS/Tween, 4 times for 5 minutes each. After the last wash, the blot is developed by the ECL method (Amersham) or some equivalent.

Using a densitometer or graphics program (e.g. ImageQuant—Molecular Dynamics), each blot is scanned. The Tie-2 band is isolated and "boxed out" for each lane. The pixel volume or comparable measure for each sample is analyzed. Also, an appropriate background region of the same dimensions is determined for each sample. After adjusting for background, phosphorylation is expressed as the ratio of phosphotyrosine staining, relative to the untreated control.

Angiogenesis in Vivo Model

Measurement of Angiogenesis In Vivo—Murine Air Pouch Granuloma Model:

Described below a model of inflammatory angiogenesis used to show that inhibition of Tie2 will stop the tissue destruction of excessive or inappropriate proliferation of blood vessels. The murine airpouch granuloma model of chronic inflammation (Kimura et al., 1985, J. Pharmacobio-Dyn., 8:393–400; Colville-Nash et al., 1995, *J. Pharm. and Exp. Ther.*, 274:1463–1472) whose disclosure is incorporated herein by reference in its entirety, is characterized by inflammatory cell influx, fibrous tissue proliferation and intense angiogenesis. It is representative of inflammatory angiogenesis and demonstrates that the angiogenic component can be pharmacologically modulated independently of granuloma growth and size. In addition, angiogenesis can be accurately quantitated by a vascular casting method.

Day 1, mice are anesthetized using Aerrane (isoflurane) gas (5%) or other approved methods, after which 3 mls of air is injected into the dorsal subcutaneous tissue using a 27 g needle. Mice are allowed to recover.

Day 0, mice are again anesthetized using Aerrane or other approved methods, once anesthetized 0.5 ml of Freunds complete adjuvant with 0.1% v/v croton oil is injected into the air pouch formed on Day –1. The animals also begin their dosing regime (number of day's dependent upon study) with the animals typically receiving compound in 0.2 ml N,N, Dimethyl Acetoacetamide(DMA) (Sigma, St. Louis, Mo.)/Cremephor El (Sigma, St. Louis, Mo.), saline (10/10/ 80) or other appropriate vehicle. The animals are allowed to recover and all subsequent dosing is performed on the animals in the absence of anesthetics.

Days 1–5, animals are dosed according to schedule.

On Day 6 the animals are again anesthetized after which a vascular cast is made (Kimura et al., 1986, *J.Pharmacobio-Dyn.*, 9:442–446); this involves a 1 ml tail vein i.v. injection of a Carmine Red (10%) (Sigma, St. Louis, Mo.)/ gelatin (5%) (Sigma, St. Louis, Mo.) solution. The animals are then sacrificed by lethal dose of anesthesia and chilled at 4° C. for 2 hours prior to the removal of the granuloma tissue.

When the granuloma is removed it is weighed and then dried for 3 days at 45° C. and reweighed. The dried tissue is then digested in 0.9 ml of a 0.05M phosphate buffer pH 7.0 containing 12 U/ml$^{-1}$ pipain (Sigma, St. Louis, Mo.) and 0.33 g/L$^{-1}$ N-acetyl-1-Cysteine (Sigma, St. Louis, Mo.) at 57° C. for 3 days. After 3 days digestion the carmine red is solublized by the addition of 0.1 ml 5 mM NaOH. Samples are centrifuged and then filtered using 0.2 um acrodiscs. The carmine content is then determined against a carmine red standard curve (0.5 to 2 mg/ml) generated in extracted tissue from non carmine treated animals and read at 490 nm. Sample and standard values are determined typically using DeltaSoft Elisa analysis software (Biometallics Inc., Princeton, N.J.). The carmine content is then used to determine the vascular indexes for the various treatments, vascular index being the mg carmine dye/gm dry tissue.

The effect of compounds on vascular density was typically measured for 6 days after induction of the granuloma. This time point has been determined to be at or near the peak of angiogenesis. As a positive control medroxyprogesterone, an angiostatic steroid (Gross et al., 1981, Proc. Natl. Acad. Sci. USA, 78:1176–1180), whose disclosure is hereby incorporated by reference in its entirety, was utilized. This control demonstrated a maximum reduction of 50% in this model. Medroxyprogesterone had no effect on granuloma size as measured by dry weight.

Angiogenesis Model—In Vivo

Measurement of Angiogenesis In Vivo—Matrigel Model:

Angiogenesis is modeled in-vivo by placing an extra-cellular matrix gel, beneath the skin of a mouse for approximately one week, and then employing several measures to quantitate angiogenic invasion of the gel (Biancone,L, et. al. Development of Inflammatory Angiogenesis by Local Stimulation of Fas In Vivo. J. Exp. Med. 186:147, 1997.). Briefly, reduced growth factor, endotoxin free Matrigel® (Becton-Dickinson, Bedford, Mass.) is a gel at low temperatures. Antibodies or known angiogenic agents are mixed with the gel, such that they do not constitute more than 2% of the total volume. Eight week old or older, C57 female mice are administered 0.5 ml of the Matrigel® by dorsal subcutaneous injection through chilled syringes. At physiological temperature, the liquid Matrigel® rapidly forms a solid and cohesive gel. During the course of the experiment, mice receive test compounds or controls administered as described above. After six days, the mice are sacrificed and the Matrigel® plugs recovered. Angiogenesis is quantitated by analyzing the hemoglobin content of the gel by the method of Drabkin (Drabkin,D L and Austin,J H: Spectrophotometric Studies II. Preparations from washed blood cells; nitric oxide hemoglobin and sulfhemoglobin. J Biol Chem 112:51, 1935.)(Sigma, St. Louis, Mo.), or by staining and quantitating blood-vessel with CD31 staining as described above.

Synthetic Chemistry

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment, unless otherwise indicated. ¹H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Flash chromatography is run over Merck Silica gel 60 (230–400 mesh).

EXAMPLE 1

(2-(4-(6-methoxynapthalen-2-yl)-5-pyridin-4-yl-1H-imidazol-2-yl)-2-methyl-propyl)-carbamic acid tert-butyl ester

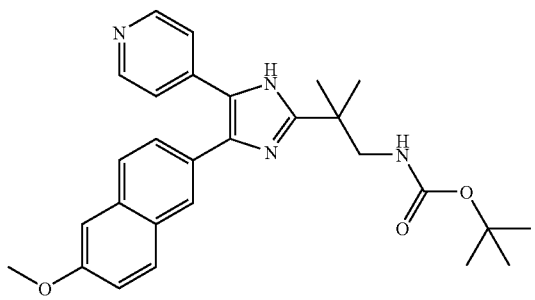

a) 6-Methoxy-napthylene-2-carboxylic acid-N-methoxy-N-methyl-amide

A suspension of 6-methoxynapthoic acid (10.95 grams (hereinafter "g"), 0.05 moles (herein after "mol"), triethylamine (29.8 milliliters (hereinafter "mL" or "ml")), 0.2 mol) in dichloromethane (150 ml) was cooled to 0° C. and slowly thionyl chloride (4.35 ml) was added, upon which the solution became brown and homogenous. The ice bath was removed and continued stirring at room temperature for about 1 hour (hereinafter "h") at which point T methoxymethylamine hydrochloride (7.02 g, 0.06 mol) was added. The mixture was stirred at room temperature for 3 hours. The solution was concentrated and the residue was partitioned between dichloromethane and saturated potassium carbonate solution. The organic layer was separated, washed with brime dried over anhydrous magnesium sulphate, filtered and concentrated at reduced pressure to give the title compound (9.65 g, 73%) as a brown solid; MS(ES) m/e 246 [M+H]⁺.

b) 4-t-Butyldimethylsiloxymethylpyridine

4-Pyridylcarbinol (8.5 g, 0.08 mol) was dissolved in a 9:1 mixture of N,N-dimethylformamide and dichloromethane (150 mL). t-Butyldimethylsilylchloride (13 g, 0.09 mol) and imidazole (6.4 g, 0.09 mol) were added and the solution was stirred for 12 hours at room temperature. The reaction mixture was concentrated at reduced pressure and the residue was partitioned between ethyl acetate and water. The organic layer was separated, dried over anhydrous magnesium sulphate, filtered and concentrated at reduced pressure to give the title compound (17.4 g, 92%) as a colorless oil; MS(ES) m/e 244 [M+H]⁺.

c) 1-(t-Butyl-dimethylsiloxy)-2-(6-methoxy-naphthalen-2-yl)-1-pyridin-4-yl-ethan-2-one To a stirring solution of diisopropylamine (5.01 mL, 0.035 mol) in tetrahydrofuran (50 mL) at 0° C. was added n-butyl lithium 15.5 mL, 0.039 mol) to generate lithium diisopropylamide in situ. To the cooled −78° C. LDA solution was added 4-t-butyldimethylsiloxypyridine (7.84 g, 0.035 mol) and stirring was continued for 30 minutes at which time 6-methoxynapthylene-2-carboxylic acid-N-methoxy-N-methyl-amide (5.51 g, 0.023 mol) was added. The reaction was gradually allowed to warm to room temperature. The reaction mixture was extracted with ethyl acetate and the organic layers were combined, dried over anhydrous magnesium sulphate, filtered and concentrated at reduced pressure. The title compound was purified by flash chromatography and isolated as a yellow solid; MS(ES) m/e 377 [M+H]⁺.

d) (2-(4-(6-methoxy-naphthalen-2-yl)-5-pyridin-4-yl-1-imidazol-2-yl)-2-methyl-propyl)-carbamic acid tert-butyl ester Acetic acid (15 ml) was added into a mixture of (2,2-dimethyl-3-oxo-propyl)-carbamic acid tert-butyl ester (Y. Guindon et al., *J. Am. Chem. Soc.,* 1997, 119, 9289) (0.26 g, 1.2 mmol), ammonium acetate (0.98 g, 12.0 mmol), and 2-(t-butyl-dimethylsilanyloxy)-2-(6-methoxy-naphthalen-2-yl)-1-pyridin-4-yl-ethanone (0.26 g, 0.6 mmol). The resulting solution was heated at 90° C. overnight, then cooled to 0° C., and NH₄OH was added to the solution slowly with stirring. The resulting precipitate was filtered, and dried to yield the title compound; MS(ES) m/e 472 [M+H]⁺.

EXAMPLE 2

2-(4-(6-methoxy-napthalen-2-yl)-5-pyridin-4-yl-1H-imidazol-2-yl)-2-methyl-propylamine

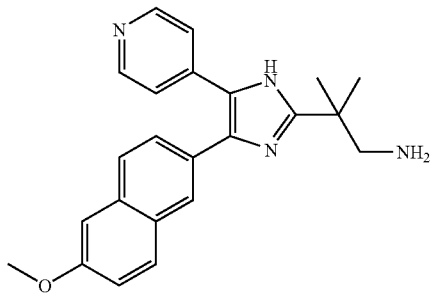

The product of Example 1 (200 milligrams (hereinafter "mg"), 0.4 millimoles (hereinafter "mmol")) was dissolved in a 1:1 mixture of trifluoroacetic acid and dichloromethane (5 mL) and stirred at room temperature for 4 hours. The solvents were concentrated at reduced pressure. The crude product was purified by column chromatography to afford the title compound (50 mg, 32%). MS(ES) m/e 373 [M+H]$^+$.

EXAMPLE 3 n-Propyl-(2-(4-(6-methoxy-napthalen-2-yl)-5-pyridin-4-yl-1H-imidazol-2-yl)-2-methyl-propyl)-(3-methylsulfanyl-propyl)-amine

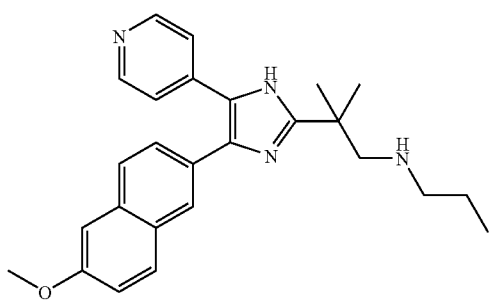

A solution of Example 2 (20 mg, 0.05 mmol) in N,N-dimethylformamide (2 ml) was treated with potassium carbonate (10 mg, 0.07 mmol) and 1-bromopropane (9 mg, 0.07 mmol). The solution was stirred at room temperature for 4 hours. The mixture was diluted with water and extracted with ethyl acetate. The aqueous layer was separated and extracted with additional ethyl acetate, the organic layers were combined, dried over anhydrous magnesium sulphate, filtered and concentrated at reduced pressure. The residue was chromatographed on a Gilson HPLC to give the title compound (3 mg, 13%) as a yellow solid; MS(ES+) m/e. 415 [M+H]+.

EXAMPLE 4

(2-(4-(6-methoxy-napthalen-2-yl)-5-pyridin-4-yl-1H-imidazol-2-yl)-2-methyl-propyl)-methane-sulfonamide

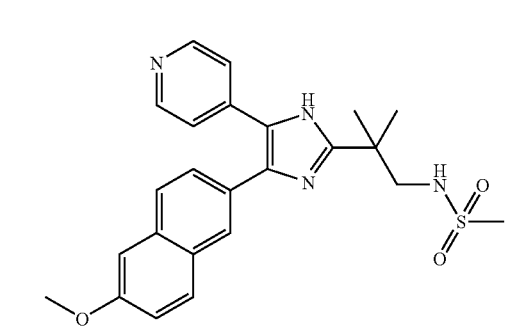

A solution of the product of Example 2 (15 mg, 0.04 mmol) in a 1:1 mixture of tetrahydrofuran and dichloromethane (2 mL) containing Hunig's base (9 μL, 0.05 mmol) was treated with methanesulfonyl chloride (4 μL, 0.05 mmol) and stirred at room temperature for 8 hours. The mixture was diluted with water and extracted with dichloromethane. The aqueous layer was separated and extracted with additional dichloromethane, the organic layers were combined, dried over anhydrous magnesium sulphate, filtered and concentrated at reduced pressure. The residue was chromatographed on a Gilson HPLC to give the title compound (8 mg, 44%) as a yellow solid; MS(ES) m/e. 451 [M+H]$^+$.

EXAMPLE 5

1,1,1-trifluoro-N-(2-(4-(6-methoxy-napthalen-2-yl)-5-pyridin-4-yl-1H-imidazol-2-yl)-2-methyl-propyl)-methanesulfonamide

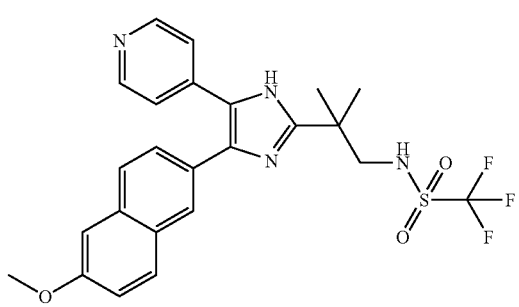

The title compound (9 mg, 33%) was prepared starting from the product of Example 2 and 1,1,1-trifluoromethane-sulfonyl chloride using the method described in Example 4; MS(ES) m/e 505 [M+H]$^+$.

EXAMPLE 6

2,2,2-trifluoro-N-(2-(4-(6-methoxy-napthalen-2-yl)-5-pyridin-4-yl-1H-imidazol-2-yl)-2-methyl-propyl)-ethanesulfonamide

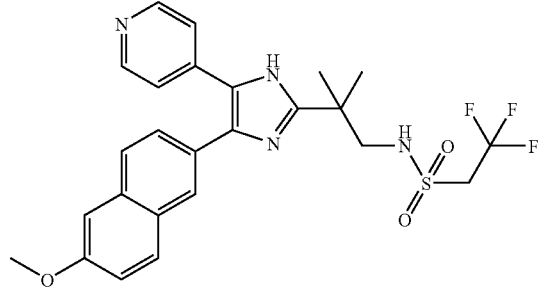

The title compound (12 mg, 43%) was prepared starting from the product of Example 2 and 2,2,2-trifluoroethanesulfonyl chloride using the method described in Example 4; MS(ES) m/e 519 [M+H]⁺.

EXAMPLE 7

(2-(4-(6-methoxy-napthalen-2-yl)-5-pyridin-4-yl-1H-imidazol-2-yl)-2-methyl-propyl)-propane-sulfonamide

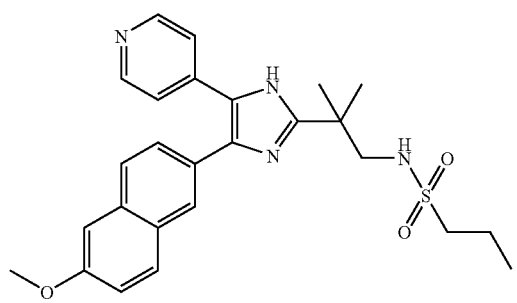

The title compound (7 mg, 27%) was prepared starting from the product of Example 2 and propanesulfonyl chloride using the method described in Example 4; MS(ES) m/e 479 [M+H]⁺.

EXAMPLE 8

3-Chloro-N-(2-(4-(6-methoxy-napthalen-2-yl)-5-pyridin-4-yl-1H-imidazol-2-yl)-2-methyl-propyl)-propanesulfonamide

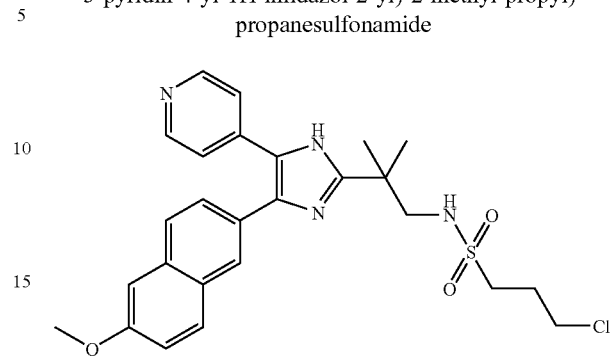

The title compound (11 mg, 40%) was prepared starting from the product of Example 2 and 3-chloro-propanesulfonyl chloride using the method described in Example 4; MS(ES) m/e 514 (M+H)⁺.

EXAMPLE 9

(2-(4-(6-methoxy-napthalen-2-yl)-5-pyridin-4-yl-1H-imidazol-2-yl)-2-methyl-propyl)-butanesulfonamide

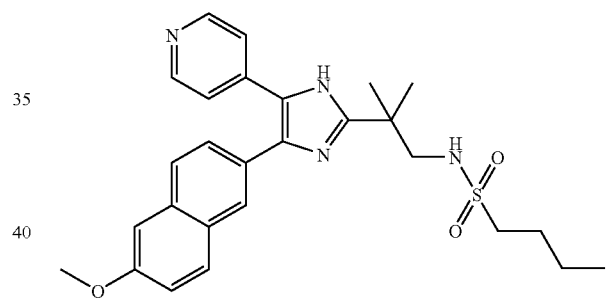

The title compound (8 mg, 30%) was prepared starting from the product of Example 2 and butanesulfonyl chloride using the method described in Example 4; MS(ES) m/e 493 [M+H]⁺.

EXAMPLE 10

1-Ethyl-3-(2-(4-(6-methoxy-napthalen-2-yl)-5-pyridin-4-yl-1H-imidazol-2-yl)-2-methyl-propyl)-urea

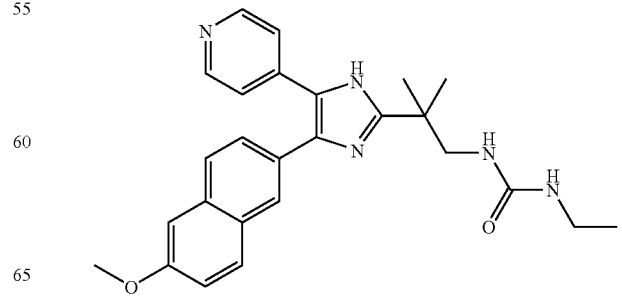

A solution of the product of Example 2 (20 mg, 0.05 mmol) in dichloromethane (2 mL) containing Hunig's base (10 μL, 0.07 mmol) was treated with ethyl isocyanate (6 μL, 0.07 mmol) and stirred at room temperature for 8 hours. The mixture was diluted with water and extracted with dichloromethane. The aqueous layer was separated and extracted with additional dichloromethane, the organic layers were combined, dried over anhydrous magnesium sulphate, filtered and concentrated at reduced pressure. The residue was chromatographed on a Gilson HPLC to give the title compound (12 mg, 50%) as a yellow solid; MS(ES) m/e 444 [M+H]+.

EXAMPLE 11

1-(2-Chloroethyl)-3-(2-(4-(6-methoxy-napthalen-2-yl)-5-pyridin-4-yl-1H-imidazol-2-yl)-2-methyl-propyl)-urea

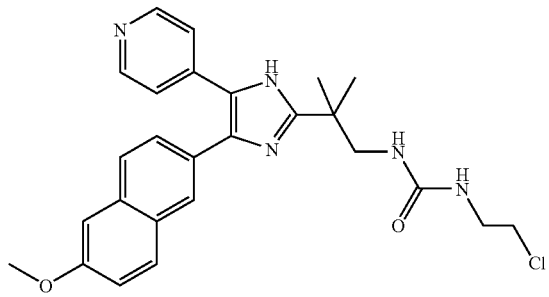

The title compound (13 mg, 51%) was prepared starting from the product of Example 2 and 3-chloroethyl isocyanate using the method described in Example 10; MS(ES) m/e 478 [M+H]+.

EXAMPLE 12

1-n-Propyl-3-(2-(4-(6-methoxy-napthalen-2-yl)-5-pyridin-4-yl-1H-imidazol-2-yl)-2-methyl-propyl)-urea

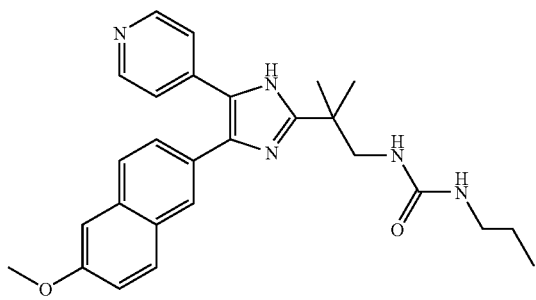

The title compound (12 mg, 49%) was prepared starting from the product of Example 2 and n-propyl isocyanate using the method described in Example 10; MS(ES) m/e 458 [M+H]+.

EXAMPLE 13

1-Isopropyl-3-(2-(4-(6-methoxy-napthalen-2-yl)-5-pyridin-4-yl-1H-imidazol-2-yl)-2-methyl-propyl)-urea

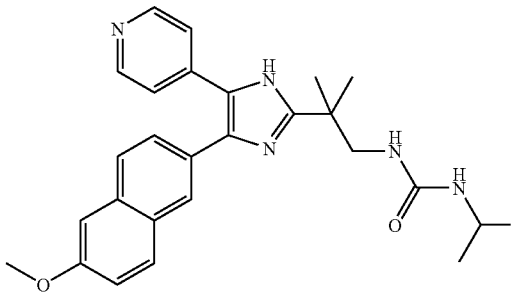

The title compound (12 mg, 49%) was prepared starting from the product of Example 2 and n-propyl isocyanate using the method described in Example 10; MS(ES) m/e 458 [M+H]+.

EXAMPLE 14

1-tert-Butyl-3-(2-(4-(6-methoxy-napthalen-2-yl)-5-pyridin-4-yl-1H-imidazol-2-yl)-2-methyl-propyl)-urea

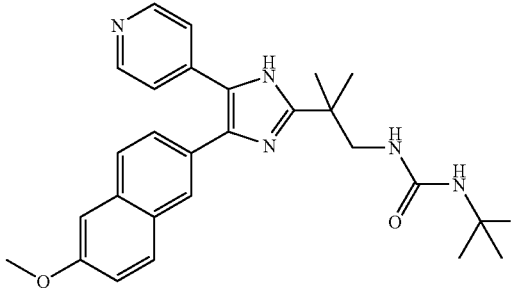

The title compound (10 mg, 39%) was prepared starting from the product of Example 2 and tert-butyl isocyanate using the method described in Example 10; MS(ES) m/e 472 [M+H]+.

EXAMPLE 15

1-Methylformyl-3-(2-(4-(6-methoxy-napthalen-2-yl)-5-pyridin-4-yl-1H-imidazol-2-yl)-2-methyl-propyl)-urea

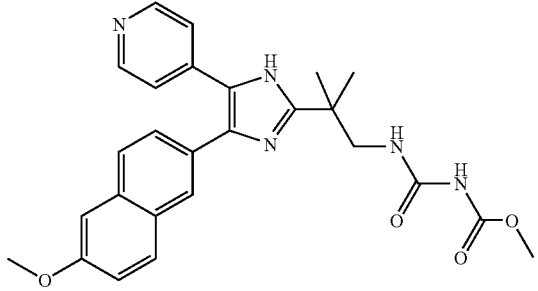

The title compound (13 mg, 51%) was prepared starting from the product of Example 2 and methylformyl isocyanate using the method described in Example 4; MS(ES) m/e 474 [M+H]⁺.

EXAMPLE 16

1-(3,5-Dimethyl-isoxazol-4-yl)-3-(2-(4-(6-methoxy-napthalen-2-yl)-5-pyridin-4-yl-1H-imidazol-2-yl)-2-methyl-propyl)-urea

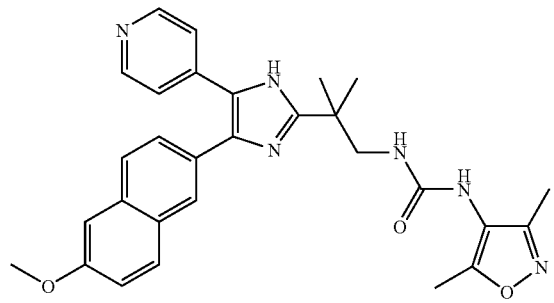

The title compound (11 mg, 40%) was prepared starting from the product of Example 2 and tert-butyl isocyanate using the method described in Example 10; MS(ES) m/e 511 [M+H]⁺.

EXAMPLE 17

1-n-Propyl-3-(2-(4-(6-methoxy-napthalen-2-yl)-5-pyridin-4-yl-1H-imidazol-2-yl)-2-methyl-propyl)-thiourea

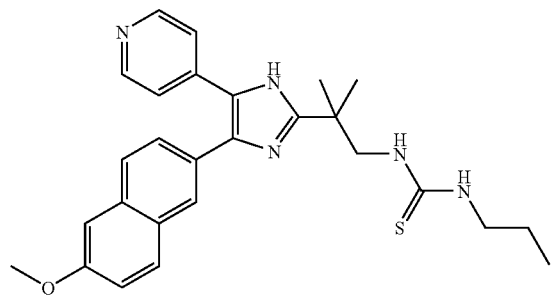

The title compound (7 mg, 28%) was prepared starting from the product of Example 2 and n-propyl thioisocyanate using the method described in Example 10; MS(ES) m/e 474 [M+H]⁺.

EXAMPLE 18

1-n-Butyl-3-(2-(4-(6-methoxy-napthalen-2-yl)-5-pyridin-4-yl-1H-imidazol-2-yl)-2-methyl-propyl)-thiourea

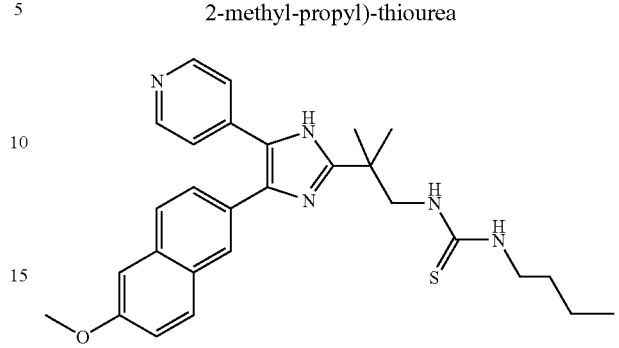

The title compound (8 mg, 31%) was prepared starting from the product of Example 2 and n-butyl thioisocyanate using the method described in Example 10; MS(ES) m/e 488 [M+H]⁺.

EXAMPLE 19

1-Isopropyl-3-(2-(4-(6-methoxy-napthalen-2-yl)-5-pyridin-4-yl-1H-imidazol-2-yl)-2-methyl-propyl)-thiourea

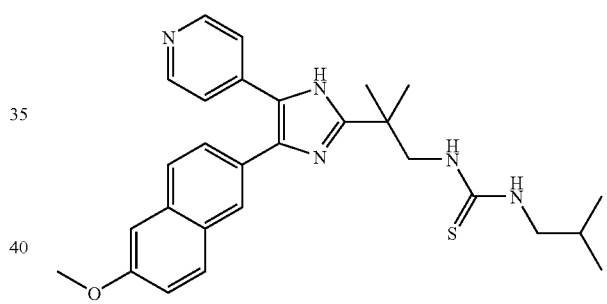

The title compound (6 mg, 23%) was prepared starting from the product of Example 2 and sec-butyl thioisocyanate using the method described in Example 10; MS(ES) m/e 488 [M+H]⁺.

EXAMPLE 20

1-Ethyl-3-(2-(4-(6-methoxy-napthalen-2-yl)-5-pyridin-4-yl-1H-imidazol-2-yl)-2-methyl-propyl)-thiourea

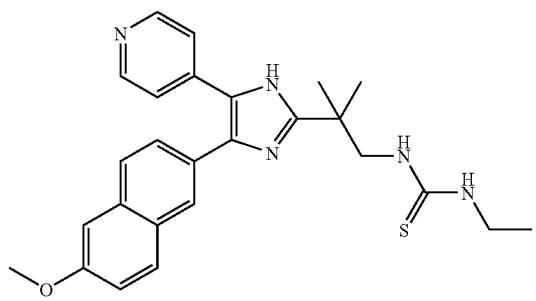

The title compound (12 mg, 49%) was prepared from Example 2 and ethyl thioisocyanate using the method described in Example 10. MS(ES+) m/e 460 [M+H]+.

EXAMPLE 21

1-Methyl-3-(2-(4-(6-methoxy-napthalen-2-yl)-5-pyridin-4-yl-1H-imidazol-2-yl)-2-methyl-propyl)-thiourea

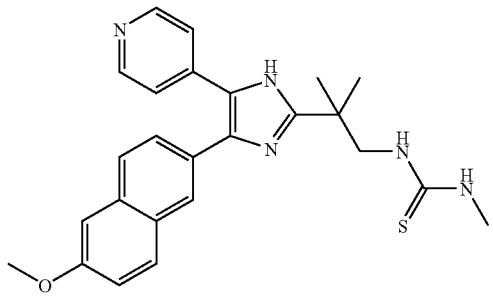

The title compound (8 mg, 30%) was prepared from Example 2 and methyl thioisocyanate using the method described in Example 10. MS(ES+) m/e 446 [M+H]+.

EXAMPLE 22

1-(2-(4-(6-methoxy-napthalen-2-yl)-5-pyridin-4-yl-1H-imidazol-2-yl)-2-methyl-propyl)-3-(2-methoxy-ethyl)-thiourea

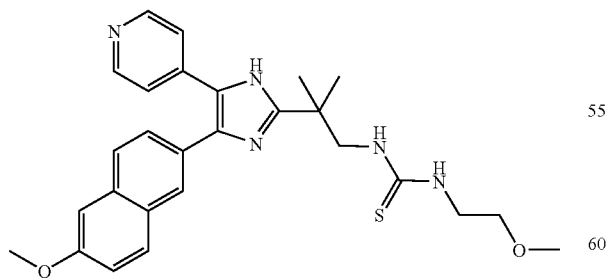

The title compound (7 mg, 27%) was prepared from Example 2 and 2-methoxyethyl isothiocyanate using the method described in Example 10. MS(ES+) m/e 490 [M+H]+.

EXAMPLE 23

1-(2-(4-(6-methoxy-napthalen-2-yl)-5-pyridin-4-yl-1H-imidazol-2-yl)-2-methyl-propyl)-3-(2-morpholin-4-yl-ethyl)-thiourea

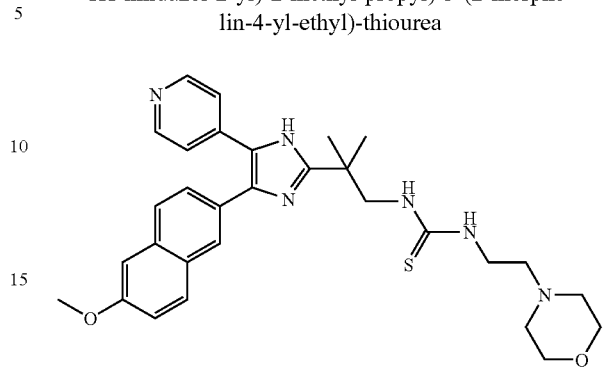

The title compound (10 mg, 34%) was prepared from Example 2 and sec-butyl thioisocyanate using the method described in Example 10. MS(ES+) m/e 545 [M+H]+.

EXAMPLE 24

1-(2-(4-(6-methoxy-napthalen-2-yl)-5-pyridin-4-yl-1H-imidazol-2-yl)-2-methyl-propyl)-3-(2-piperidin-4-yl-ethyl)-thiourea

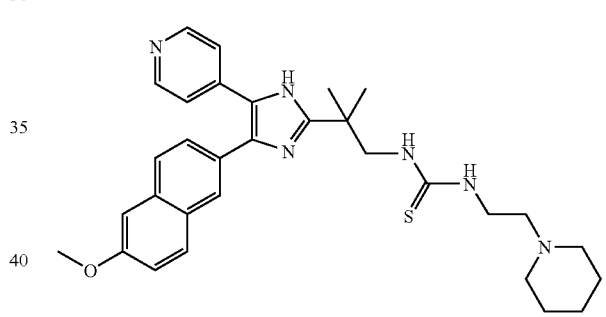

The title compound (9 mg, 31%) was prepared from Example 2 and sec-butyl thioisocyanate using the method described in Example 10. MS(ES+) m/e 543 [M+H]+.

EXAMPLE 25

Cyclohexylmethyl-(2-(4-(6-methoxy-napthalen-2-yl)-5-pyridin-4-yl-1H-imidazol-2-yl)-2-methyl-propyl)-amine

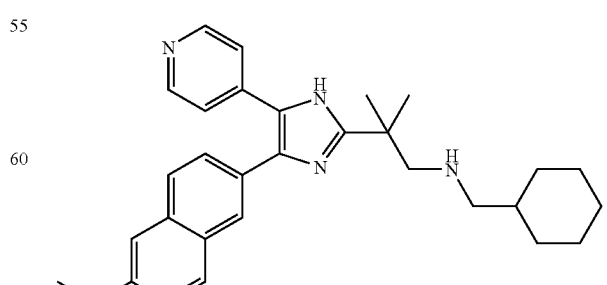

A solution of the product of Example 2 (20 mg, 0.05 mmol) in dichloromethane (2 mL) was treated with cyclohexaldehyde (3 mg, 0.07 mmol) and sodium trimethoxyborohydride (9 mg, 0.07 mmol). The solution was stirred at room temperature for 4 hours. The mixture was diluted with water and extracted with ethyl acetate. The aqueous layer was separated and extracted with additional ethyl acetate, the organic layers were combined, dried over anhydrous magnesium sulphate, filtered and concentrated at reduced pressure. The residue was chromatographed on a Gilson HPLC to give the title compound (10 mg, 40%) as a yellow solid; MS(ES) m/e 469 [M+H]$^+$.

EXAMPLE 26

Bis-n-butyl-(2-(4-(6-methoxy-napthalen-2-yl)-5-pyridin-4-yl-1H-imidazol-2-yl)-2-methyl-propyl)-amine

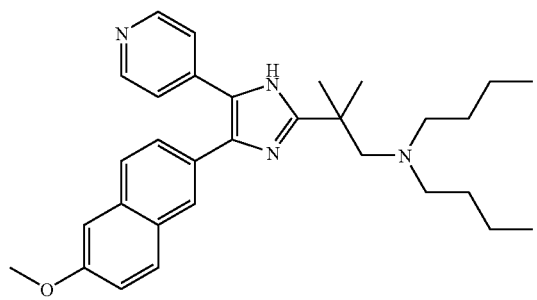

The title compound (12 mg, 47%) was prepared starting from the product of Example 2 and butyraldehyde using the method described in Example 25; MS(ES) m/e 485 [M+H]$^+$.

EXAMPLE 27

Bis-cyclohexylmethyl-(2-(4-(6-methoxy-napthalen-2-yl)-5-pyridin-4-yl-1H-imidazol-2-yl)-2-methyl-propyl)-amine

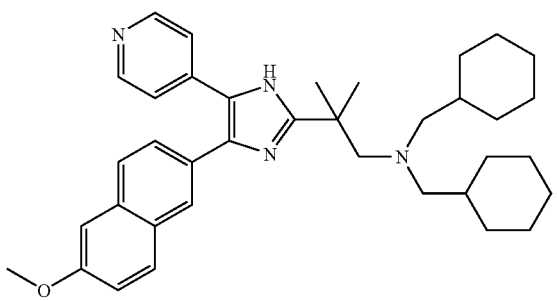

The title compound (4 mg, 13%) was prepared starting from the product of Example 2 and cyclohexylaldehyde using the method described in Example 25; MS(ES) m/e 565 [M+H]$^+$.

EXAMPLE 28

(2-(4-(6-methoxy-napthalen-2-yl)-5-pyridin-4-yl-1H-imidazol-2-yl)-2-methyl-propyl)-(3-methylsulfanyl-propyl)-amine

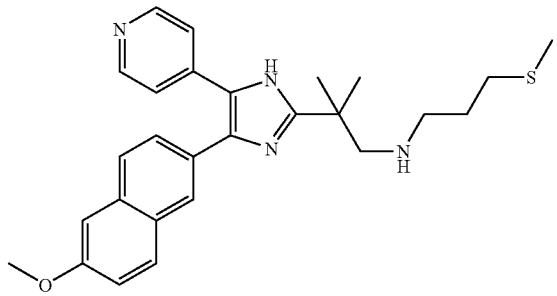

The title compound (4 mg, 16%) was prepared starting from the product of Example 2 and 1-thiomethylproprionaldehyde using the method described in Example 25; MS(ES) m/e 461 [M+H]$^+$.

EXAMPLE 29

(2-(4-(6-methoxy-napthalen-2-yl)-5-pyridin-4-yl-1H-imidazol-2-yl)-2-methyl-propyl)-bis-(3-methylsulfanyl-propyl)-amine

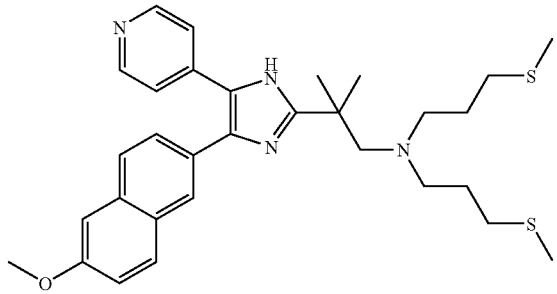

The title compound (11 mg, 46%) was prepared starting from the product of Example 2 and 1-thiomethylproprionaldehyde using the method described in Example 25; MS(ES) m/e 549 [M+H]$^+$.

EXAMPLE 30

Isobutyl-(2-(4-(6-methoxy-napthalen-2-yl)-5-pyridin-4-yl-1H-imidazol-2-yl)-2-methyl-propyl)-(3-methylsulfanyl-propyl)-amine

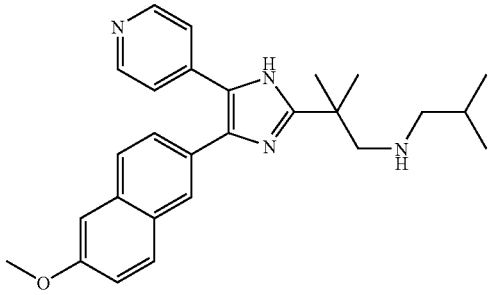

The title compound (11 mg, 48%) was prepared starting from the product of Example 2 and isoproprionaldehyde using the method described in Example 25; MS(ES) m/e 429 [M+H]+.

EXAMPLE 31

Bis-isobutyl-(2-(4-(6-methoxy-napthalen-2-yl)-5-pyridin-4-yl-1H-imidazol-2-yl)-2-methyl-propyl)-(3-methylsulfanyl-propyl)-amine

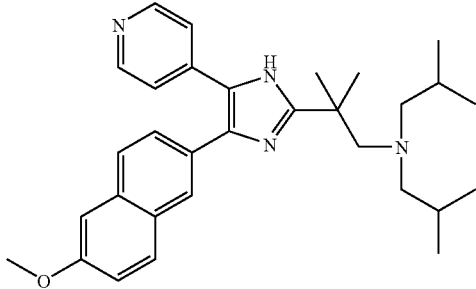

The title compound (11 mg, 42%) was prepared starting from the product of Example 2 and i-propionaldehyde using the method described in Example 25; MS(ES) n/e 485 [M+H]+.

EXAMPLE 32

(2,2-Dimethylpropyl)-(2-(4-(6-methoxy-napthalen-2-yl)-5-pyridin-4-yl-1H-imidazol-2-yl)-2-methyl-propyl)-(3-methylsulfanyl-propyl)-amine

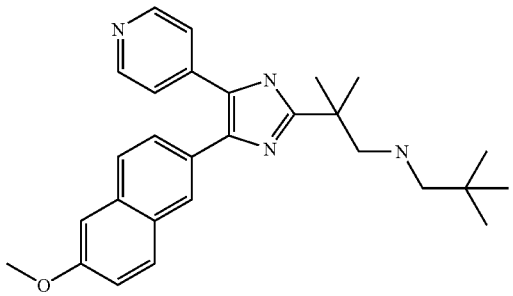

The title compound (16 mg, 67%) was prepared starting from the product of Example 2 and t-butyraldehyde using the method described in Example 25; MS(ES) m/e 443 [M+H]+.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:
1. A compound of formula (I):

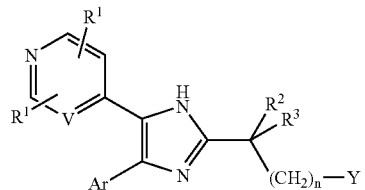

wherein
V is CH;
Ar is a napth-2-yl, napth-1-yl ring, which ring may be optionally substituted one or more times, independently, in any ring by halogen, $C_{1-6}$alkyl, aryl, aryl$C_{1-6}$alkyl, cycloalkyl, cycloalkyl $C_{1-6}$alkyl, $C_{1-6}$alkoxy$C_{1-6}$alkyl, halosubstituted $C_{1-6}$alkyl, aryl$C_{1-6}$alkoxy, $(CR^{13}R^{14})_tOR^{12}$, nitro, cyano, $(CR^{13}R^{14})_tNR^{10}R^{11}$, $(CR^{13}R^{14})_tNR^{10}C(Z)R^{12}$, $(CR^{13}R^{14})_tC(Z)NR^{10}R^{11}$, $(CR^{13}R^{14})_tCOR^{12}$, $(CR^{13}R^{14})_tZC(Z)R^{12}$, $(CR^{13}R^{14})_tC(Z)OR^{12}$, $(CR^{13}R^{14})_tC(O)NR^{10}R^{11}$, $(CR^{13}R^{14})_tNR^{10}C(Z)NR^{10}R^{11}$, $(CR^{13}R^{14})_tNR^{10}C(=NH)NR^{10}R^{11}$, $(CR^{13}R^{14})_tC(=NH)-NR^{10}R^{11}$, $(CR^{13}R^{14})_tNR^{10}S(O)_2R^8$, $(CR^{13}R^{14})_tS(O)_2NR^{10}R^{11}$, $(CR^{13}R^{14})_tS(O)_mR^{12}$;
Y is $NR^{10}R^{11}$, $NR^{10}C(Z)NR^{10}R^{11}$, $NR^{10}C(Z)NR^{10}C(Z)OR^{11}$, or $NR^{10}SO_2R^{11}$;
n is 1, 2, 3 or 4;
m is 0, 1, or 2
t is 0, or an integer having a value of 1 to 10;
X is O, $CH_2$, S or NH;
Z is oxygen or sulfur;
$R^1$ is independently hydrogen, $X-R^4$, halogen, hydroxy, $C_{1-6}$ alkyl, $C_{1-6}$alkylsulfinyl, $CH_2OR^5$, amino, mono or di-$C_{1-6}$alkylamino, $N(R^6)C(O)R^7$, or $N(R^6)S(O)_2R^8$;
$R^2$ and $R^3$ independently represent optionally substituted $C_{1-6}$alkyl, or $R^2$ and $R^3$ together with the carbon atom to which they are attached form an optionally substituted $C_{3-7}$cycloalkyl or $C_{5-7}$ cycloalkenyl ring, and wherein the alkyl, cycloalkyl or cycloalkenyl moieties are optionally substituted, one or more times, independently, by the group selected from halogen, $C_{1-6}$alkyl, aryl, aryl$C_{1-6}$alkyl, cycloalkyl, cycloalkyl $C_{1-6}$alkyl, $C_{1-6}$alkoxy$C_{1-6}$alkyl, halosubstituted $C_{1-6}$alkyl, aryl$C_{1-6}$alkoxy, $(CR^{13}R^{14})_tOR^{12}$, nitro, cyano, $(CR^{13}R^{14})_t NR^{10}R^{11}$, $(CR^{13}R^{14})_tNR^{10}C(Z)R^{12}$, $(CR^{13}R^{14})_tC(Z)NR^{10}R^{11}$, $(CR^{13}R^{14})_tCOR^{12}$, $(CR^{13}R^{14})_tZC(Z)R^{12}$, $(CR^{13}R^{14})_tC(Z)OR^{12}$, $(CR^{13}R^{14})_tC(O)NR^{10}R^{11}$, $(CR^{13}R^{14})_tNR^{10}C(Z)NR^{10}R^{11}$, $(CR^{13}R^{14})_tNR^{10}C(=NH)NR^{10}R^{11}$, $(CR^{13}R^{14})_tC(=NH)-NR^{10}R^{11}$, $(CR^{13}R^{14})_tNR^{10}S(O)_2R^8$, $(CR^{13}R^{14})_tS(O)_2NR^{10}R^{11}$, $S(O)_mR^{12}$;
$R^4$ is independently $C_{1-6}$alkyl, aryl, or aryl$C_{1-6}$alkyl, and wherein any of these moieties may be optionally substituted one or more times, independently, by a group selected from halogen, $C_{1-6}$alkyl, aryl, aryl$C_{1-6}$alkyl, cycloalkyl, cycloalkyl $C_{1-6}$alkyl, $C_{1-6}$alkoxy$C_{1-6}$alkyl, halosubstituted $C_{1-6}$alkyl, aryl$C_{1-6}$alkoxy, $(CR^{13}R^{14})_tOR^{12}$, nitro, cyano, $(CR^{13}R^{14})_tNR^{10}R^{11}$, $(CR^{13}R^{14})_t$ NR$^{10}$C(Z)R$^{12}$, (CR$^{13}$R$^{14}$)$_t$C(Z)NR$^{10}$R$^{11}$, (CR$^{13}$R$^{14}$)$_t$COR$^{12}$, (CR$^{13}$R$^{14}$)$_t$ZC(Z)R$^{12}$, (CR$^{13}$R$^{14}$)$_t$C(Z)OR$^{12}$, (CR$^{13}$R$^{14}$)$_t$C(O)NR$^{10}$R$^{11}$, (CR$^{13}$R$^{14}$)$_t$NR$^{10}$C(Z)NR$^{10}$R$^{11}$, (CR$^{13}$R$^{14}$)$_t$NR$^{10}$C(=NH)NR$^{10}$R$^{11}$, (CR$^{13}$R$^{14}$)$_t$C(=NH)—NR$^{10}$R$^{11}$, (CR$^{13}$R$^{14}$)$_t$NR$^{10}$S(O)$_2$R$^8$, (CR$^{13}$R$^{14}$)$_t$S(O)$_2$NR$^{10}$R$^{11}$, or S(O)$_m$R$^{12}$;

R$^5$ is hydrogen, C(Z)R$^{12}$ or optionally substituted C$_{1-6}$alkyl, optionally substituted aryl, optionally substituted arylC$_{1-6}$alkyl, or S(O)$_2$R$^8$; and wherein the moieties may be optionally substituted one or more times, independently, by a group selected from halogen, C$_{1-6}$alkyl, aryl, arylC$_{1-6}$alkyl, cycloalkyl, cycloalkyl C$_{1-6}$alkyl, C$_{1-6}$alkoxyC$_{1-6}$alkyl, halosubstituted C$_{1-6}$alkyl, arylC$_{1-6}$alkoxy, (CR$^{13}$R$^{14}$)$_t$OR$^{12}$, nitro, cyano, (CR$^{13}$R$^{14}$)$_t$NR$^{10}$R$^{11}$, (CR$^{13}$R$^{14}$)$_t$NR$^{10}$C(Z)R$^{12}$, (CR$^{13}$R$^{14}$)$_t$C(Z)NR$^{10}$R$^{11}$, (CR$^{13}$R$^{14}$)$_t$COR$^{12}$, (CR$^{13}$R$^{14}$)$_t$ZC(Z)R$^{12}$, (CR$^{13}$R$^{14}$)$_t$C(Z)OR$^{12}$, (CR$^{13}$R$^{14}$)$_t$C(O)NR$^{10}$R$^{11}$, (CR$^{13}$R$^{14}$)$_t$NR$^{10}$C(Z)NR$^{10}$R$^{11}$, (CR$^{13}$R$^{14}$)$_t$NR$^{10}$C(=NH)NR$^{10}$R$^{11}$, (CR$^{13}$R$^{14}$)$_t$C(=NH)—NR$^{10}$R$^{11}$, (CR$^{13}$R$^{14}$)$_t$NR$^{10}$S(O)$_2$R$^8$, (CR$^{13}$R$^{14}$)$_t$S(O)$_2$NR$^{10}$R$^{11}$, or S(O)$_m$R$^{12}$;

R$^6$ is hydrogen or C$_{1-6}$alkyl;

R$^7$ is hydrogen, C$_{1-6}$alkyl, C$_{3-7}$cycloalkyl, aryl, or arylC$_{1-6}$alkyl;

R$^8$ is C$_{1-6}$alkyl, C$_{3-7}$cycloalkyl, aryl, or arylC$_{1-6}$alkyl;

R$^9$ is hydrogen, C$_{1-4}$alkyl, C$_{3-7}$cycloalkyl or aryl;

R$^{10}$ and R$^{12}$ are independently selected from hydrogen, C$_{1-6}$alkyl, C$_{3-7}$cycloalkyl, C$_{3-7}$cycloalkyl C$_{1-6}$alkyl, aryl, arylC$_{1-6}$alkyl any of which moieties may be optionally substituted one or more times, independently, by a group selected from halogen, C$_{1-6}$alkyl, aryl, arylC$_{1-6}$alkyl, cycloalkyl, cycloalkyl C$_{1-6}$alkyl, C$_{1-6}$alkoxyC$_{1-6}$alkyl, halosubstituted C$_{1-6}$alkyl, arylC$_{1-6}$alkoxy, (CR$^{13}$R$^{14}$)$_t$OR$^{12}$, nitro, cyano, (CR$^{13}$R$^{14}$)$_t$NR$^{10}$R$^{11}$, (CR$^{13}$R$^{14}$)$_t$NR$^{10}$C(Z)R$^{12}$, (CR$^{13}$R$^{14}$)$_t$C(Z)NR$^{10}$R$^{11}$, (CR$^{13}$R$^{14}$)$_t$COR$^{12}$, (CR$^{13}$R$^{14}$)$_t$ZC(Z)R$^{12}$, (CR$^{13}$R$^{14}$)$_t$C(Z)OR$^{12}$, (CR$^{13}$R$^{14}$)$_t$C(O)NR$^{10}$R$^{11}$, (CR$^{13}$R$^{14}$)$_t$NR$^{10}$C(Z)NR$^{10}$R$^{11}$, (CR$^{13}$R$^{14}$)$_t$NR$^{10}$C(=NH)NR$^{10}$R$^{11}$, (CR$^{13}$R$^{14}$)$_t$C(=NH)—NR$^{10}$OR$^{11}$, (CR$^{13}$R$^{14}$)$_t$NR$^{10}$S(O)$_2$R$^8$, (CR$^{13}$R$^{14}$)$_t$S(O)$_2$NR$^{10}$R$^{11}$, or S(O)$_m$R$^{12}$;

R$^{11}$ is hydrogen, C$_{1-6}$alkyl, C$_{3-7}$cycloalkyl, C$_{3-7}$cycloalkyl C$_{1-6}$alkyl, aryl, or arylC$_{1-6}$alkyl, any of which moieties may be optionally substituted one or more times, independently, by the group selected from halogen, C$_{1-6}$alkyl, aryl, arylC$_{1-6}$alkyl, cycloalkyl, cycloalkyl C$_{1-6}$alkyl, C$_{1-6}$alkoxy-C$_{1-6}$alkyl, halosubstituted C$_{1-6}$alkyl, arylC$_{1-6}$alkoxy, (CR$^{13}$R$^{14}$)$_t$OR$^{12}$, nitro, cyano, (CR$^{13}$R$^{14}$)$_t$NR$^{10}$R$^{11}$, (CR$^{13}$R$^{14}$)$_t$NR$^{10}$C(Z)R$^{12}$, (CR$^{13}$R$^{14}$)$_t$C(Z)NR$^{10}$R$^{11}$, (CR$^{13}$R$^{14}$)$_t$COR$^{12}$, (CR$^{13}$R$^{14}$)$_t$ZC(Z)R$^{12}$, (CR$^{13}$R$^{14}$)$_t$C(Z)OR$^{12}$, (CR$^{13}$R$^{14}$)$_t$C(O)NR$^{10}$R$^{11}$, (CR$^{13}$R$^{14}$)$_t$NR$^{10}$C(Z)NR$^{10}$R$^{11}$, (CR$^{13}$R$^{14}$)$_t$NR$^{10}$C(=NH)NR$^{10}$R$^{11}$, (CR$^{13}$R$^{14}$)$_t$C(=NH)—NR$^{10}$R$^{11}$, (CR$^{13}$R$^{14}$)$_t$NR$^{10}$S(O)$_2$R$^8$, (CR$^{13}$R$^{14}$)$_t$S(O)$_2$NR$^{10}$R$^{11}$, or S(O)$_m$R$^{12}$;

R$^{13}$ and R$^{14}$ are independently hydrogen, or a C$_{1-6}$ alkyl;

or a pharmaceutically acceptable salt thereof.

2. The compound according to claim 1 wherein R$^1$ is hydrogen, or the moiety X—R$^4$.

3. A compound according to claim 2 wherein X is oxygen or NH.

4. The compound according to claim 1 wherein the Ar ring is substituted by up to 3 substituents independently selected from halo, hydroxy, hydroxy C$_{1-6}$alkyl, or C$_{1-6}$alkoxy.

5. The compound according to claim 4 wherein Ar is a napth-2-yl optionally substituted by a C$_{1-6}$alkoxy group.

6. The compound according to claim 1 wherein R$^2$ and R$^3$ independently an optionally substituted C$_{1-6}$alkyl.

7. The compound according to claim 1 wherein R$^2$ and R$^3$ together with the carbon atom to which they are attached form an optionally substituted C$_{3-7}$cycloalkyl or C$_{5-7}$cycloalkenyl ring.

8. The compound according to claim 1 which is:

2-(4-(6-methoxy-napthalen-2-yl)-5-pyridin-4-yl-1H-imidazol-2-yl)-2-methyl-propylamine;

2-(4-(6-methoxy-napthalen-2-yl)-5-pyridin-4-yl-1H-imidazol-2-yl)-2-methyl-propyl)-acetamide;

(2-(4-(6-methoxy-napthalen-2-yl)-5-pyridin-4-yl-1H-imidazol-2-yl)-2-methyl-propyl)-methanesulfonamide;

1,1,1-trifluoro-N-(2-(4-(6-methoxy-napthalen-2-yl)-5-pyridin-4-yl-1H-imidazol-2-yl)-2-methyl-propyl)-methanesulfonamide;

2,2,2-trifluoro-N-(2-(4-(6-methoxy-napthalen-2-yl)-5-pyridin-4-yl-1H-imidazol-2-yl)-2-methyl-propyl)-ethanesulfonamide;

(2-(4-(6-methoxy-napthalen-2-yl)-5-pyridin-4-yl-1H-imidazol-2-yl)-2-methyl-propyl)-propanesulfonamide;

3-Chloro-N-(2-(4-(6-methoxy-napthalen-2-yl)-5-pyridin-4-yl-1H-imidazol-2-yl)-2-methyl-propyl)-propanesulfonamide;

(2-(4-(6-methoxy-napthalen-2-yl)-5-pyridin-4-yl-1H-imidazol-2-yl)-2-methyl-propyl)-butanesulfonamide;

1-Ethyl-3-(2-(4-(6-methoxy-napthalen-2-yl)-5-pyridin-4-yl-1H-imidazol-2-yl)-2-methyl-propyl)-urea;

1-(2-Chloroethyl)-3-(2-(4-(6-methoxy-napthalen-2-yl)-5-pyridin-4-yl-1H-imidazol-2-yl)-2-methyl-propyl)-urea;

1-n-Propyl-3-(2-(4-(6-methoxy-napthalen-2-yl)-5-pyridin-4-yl-1H-imidazol-2-yl)-2-methyl-propyl)-urea;

1-Isopropyl-3-(2-(4-(6-methoxy-napthalen-2-yl)-5-pyridin-4-yl-1H-imidazol-2-yl)-2-methyl-propyl)-urea;

1-tert-Butyl-3-(2-(4-(6-methoxy-napthalen-2-yl)-5-pyridin-4-yl-1H-imidazol-2-yl)-2-methyl-propyl)-urea;

1-Methylformyl-3-(2-(4-(6-methoxy-napthalen-2-yl)-5-pyridin-4-yl-1H-imidazol-2-yl)-2-methyl-propyl)-urea;

1-n-Propyl-3-(2-(4-(6-methoxy-napthalen-2-yl)-5-pyridin-4-yl-1H-imidazol-2-yl)-2-methyl-propyl)-thiourea;

1-n-Butyl-3-(2-(4-(6-methoxy-napthalen-2-yl)-5-pyridin-4-yl-1H-imidazol-2-yl)-2-methyl-propyl)-thiourea;

1-Isopropyl-3-(2-(4-(6-methoxy-napthalen-2-yl)-5-pyridin-4-yl-1H-imidazol-2-yl)-2-methyl-propyl)-thiourea;

1-Ethyl-3-(2-(4-(6-methoxy-napthalen-2-yl)-5-pyridin-4-yl-1H-imidazol-2-yl)-2-methyl-propyl)-thiourea;

1-Methyl-3-(2-(4-(6-methoxy-napthalen-2-yl)-5-pyridin-4-yl-1H-imidazol-2-yl)-2-methyl-propyl)-thiourea;

1-(2-(4-(6-methoxy-napthalen-2-yl)-5-pyridin-4-yl-1H-imidazol-2-yl)-2-methyl-propyl)-3-(2-methoxyethyl)-thiourea;

Cyclohexylmethyl-(2-(4-(6-methoxy-napthalen-2-yl)-5-pyridin-4-yl-1H-imidazol-2-yl)-2-methyl-propyl)-amine;

Bis-n-butyl-(2-(4-(6-methoxy-napthalen-2-yl)-5-pyridin-4-yl-1H-imidazol-2-yl)-2-methyl-propyl)-amine;

Bis-cyclohexylmethyl-(2-(4-(6-methoxy-napthalen-2-yl)-5-pyridin-4-yl-1H-imidazol-2-yl)-2-methyl-propyl)-amine;

(2-(4-(6-methoxy-napthalen-2-yl)-5-pyridin-4-yl-1H-imidazol-2-yl)-2-methyl-propyl)-(3-methylsulfanyl-propyl)-amine;

(2-(4-(6-methoxy-napthalen-2-yl)-5-pyridin-4-yl-1H-imidazol-2-yl)-2-methyl-propyl)-bis-(3-methylsulfanyl-propyl)-amine;
Isobutyl-(2-(4-(6-methoxy-napthalen-2-yl)-5-pyridin-4-yl-1H-imidazol-2-yl)-2-methyl-propyl)-(3-methylsulfanyl-propyl)-amine;
Bis-isobutyl-(2-(4-(6-methoxy-napthalen-2-yl)-5-pyridin-4-yl-1H-imidazol-2-yl)-2-methyl-propyl)-(3-methylsulfanyl-propyl)-amine;
(2,2-Dimethylpropyl)-(2-(4-(6-methoxy-napthalen-2-yl)-5-pyridin-4-yl-1H-imidazol-2-yl)-2-methyl-propyl)-(3-methylsulfanyl-propyl)-amine;
n-Propyl-(2-(4-(6-methoxy-napthalen-2-yl)-5-pyridin-4-yl-1H-imidazol-2-yl)-2-methyl-propyl)-(3-methylsulfanyl-propyl)-amine;
or a pharmaceutically acceptable salt thereof.

9. A pharmaceutical composition comprising a compound according to claim 1 or a pharmaceutically acceptable salt thereof and a pharmaceutically acceptable carrier.

10. A method of treating, diabetic retinopathy, in a mammal in need thereof, which comprises administering to said mammal an effective amount of a compound according to claim 1.

11. The compound according to claim 1 wherein Ar is a naphthyl-2-yl ring.

12. The compound according to claim 11 wherein the naphthyl-2-yl ring is substituted one or more times by halo, hydroxy, $C_{1-6}$alkyl, halosubstituted $C_{1-6}$alkyl, hydroxy $C_{1-6}$alkyl, and $C_{1-6}$ alkoxy.

13. The compound according to claim 12 wherein the naphthyl-2-yl ring is substituted in the 6-position.

14. The compound according to claim 13 wherein the substituent is a $C_{1-6}$ alkoxy.

15. The compound according to claim 14 wherein the substituent is methoxy.

* * * * *